US012741014B2

(12) United States Patent
Sander et al.

(10) Patent No.: US 12,741,014 B2
(45) **Date of Patent: *Sep. 22, 2026**

(54) PHARMACEUTICAL FORMULATIONS

(71) Applicant: Novo Nordisk A/S, Bagsvaerd (DK)

(72) Inventors: Tommy Sander, Smoerum (DK); Christian Poulsen, Ballerup (DK); Rosa Rebecca Erritzoee Hansen, Koebenhavn OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 19/423,120

(22) Filed: Dec. 17, 2025

(65) Prior Publication Data

US 2026/0108587 A1 Apr. 23, 2026

Related U.S. Application Data

(63) Continuation of application No. 17/799,700, filed as application No. PCT/EP2021/053805 on Feb. 17, 2021, now Pat. No. 12,527,844.

(30) Foreign Application Priority Data

Feb. 18, 2020 (EP) .................................... 20157963
Apr. 24, 2020 (EP) .................................... 20171240
Jun. 17, 2020 (EP) .................................... 20180645
Jun. 18, 2020 (EP) .................................... 20180832
Jan. 4, 2021 (EP) .................................... 21150056
Jan. 11, 2021 (EP) .................................... 21151004
Feb. 2, 2021 (EP) .................................... 21154657

(51) Int. Cl.

| | |
|---|---|
| ***A61K 38/26*** | (2006.01) |
| ***A61K 9/00*** | (2006.01) |
| ***A61K 9/08*** | (2006.01) |
| ***A61K 31/4172*** | (2006.01) |
| ***A61K 38/17*** | (2006.01) |
| ***A61K 47/02*** | (2006.01) |
| ***A61K 47/10*** | (2017.01) |
| ***A61K 47/12*** | (2006.01) |
| ***A61K 47/18*** | (2017.01) |
| ***A61K 47/22*** | (2006.01) |
| ***A61K 47/24*** | (2006.01) |
| ***A61K 47/26*** | (2006.01) |
| ***A61M 5/19*** | (2006.01) |

(52) U.S. Cl.

CPC ............ *A61K 38/26* (2013.01); *A61K 9/0019* (2013.01); *A61K 9/08* (2013.01); *A61K 31/4172* (2013.01); *A61K 38/1703* (2013.01); *A61K 47/02* (2013.01); *A61K 47/10* (2013.01); *A61K 47/12* (2013.01); *A61K 47/183* (2013.01); *A61K 47/22* (2013.01); *A61K 47/24* (2013.01); *A61K 47/26* (2013.01); *A61M 5/19* (2013.01)

(58) Field of Classification Search

CPC ...................................................... A61K 38/26
See application file for complete search history.

(56) References Cited

U.S. PATENT DOCUMENTS

| | | | | |
|---|---|---|---|---|
| 6,136,784 | A | 10/2000 | L'Italien et al. | |
| 7,312,196 | B2 | 12/2007 | L'Italien et al. | |
| 9,133,276 | B2 | 9/2015 | Cleemann et al. | |
| 9,265,723 | B2 | 2/2016 | Sprogoe et al. | |
| 9,457,066 | B2 | 10/2016 | Rau et al. | |
| 10,335,462 | B2 | 7/2019 | Jensen | |
| 10,888,605 | B2 | 1/2021 | Moeller et al. | |
| 11,207,337 | B2 | 12/2021 | Rosenthal et al. | |
| 11,318,191 | B2 | 5/2022 | Engelund et al. | |
| 12,527,844 | B2 * | 1/2026 | Sander ................ | A61K 9/0019 |
| 2001/0043934 | A1 | 11/2001 | L'Italien et al. | |
| 2003/0092606 | A1 | 5/2003 | L'Italien et al. | |
| 2005/0143303 | A1 | 6/2005 | Quay et al. | |
| 2008/0167226 | A1 | 7/2008 | Flink et al. | |
| 2012/0136298 | A1 | 5/2012 | Bendix et al. | |
| 2013/0190230 | A1 | 7/2013 | Casadesus Smith et al. | |
| 2015/0011462 | A1 | 1/2015 | Reedtz-Runge et al. | |
| 2015/0190474 | A1 | 7/2015 | Jensen et al. | |

(Continued)

FOREIGN PATENT DOCUMENTS

| | | |
|---|---|---|
| CL | 2022002085 | 1/2023 |
| CN | 102458521 A | 5/2012 |

(Continued)

OTHER PUBLICATIONS

Yang et al.,"The diabetes drug semaglutide reduces infarct size, inflammation, and apoptosis, and normalizes neurogenesis in a rat model stroke", Neuropharmacology, Aug. 2019, vol. 158, No. 107748, pp. 1-14.

(Continued)

*Primary Examiner* — Rei Tsang Shiao
(74) *Attorney, Agent, or Firm* — Jianjie Hu

(57) ABSTRACT

Disclosed herein are an aqueous pharmaceutical formulation comprising cagrilintide and an aqueous formulation comprising semaglutide. The compositions of these two pharmaceutical formulations allow for their presentation in, and administration using, the dual-chamber medical device disclosed herein. Individuals with diseases, such as diabetes and/or obesity and/or related co-morbidities, may benefit from the co-administration of semaglutide and cagrilintide, and/or of the two liquid pharmaceutical formulations disclosed herein, using the medical device disclosed herein.

25 Claims, 3 Drawing Sheets

(56) References Cited

U.S. PATENT DOCUMENTS

| | | | |
|---|---|---|---|
| 2018/0237419 | A1 | 8/2018 | Schwink et al. |
| 2019/0134162 | A1 | 5/2019 | Hansen |
| 2023/0082544 | A1 | 3/2023 | Sander et al. |

FOREIGN PATENT DOCUMENTS

| | | | | |
|---|---|---|---|---|
| CN | 108024977 | A | | 5/2018 |
| TW | 201912147 | A | | 4/2019 |
| WO | 9850059 | A1 | | 11/1998 |
| WO | 98/55144 | A1 | | 12/1998 |
| WO | 1999/024071 | | | 5/1999 |
| WO | 99/34764 | A2 | | 7/1999 |
| WO | 9934822 | A1 | | 7/1999 |
| WO | 99/40928 | A1 | | 8/1999 |
| WO | 00/41546 | A2 | | 7/2000 |
| WO | 03/101395 | A2 | | 12/2003 |
| WO | 04/037168 | A2 | | 5/2004 |
| WO | 2005021026 | A2 | | 3/2005 |
| WO | 2006052608 | A2 | | 5/2006 |
| WO | 2006/083254 | A1 | | 8/2006 |
| WO | 2006097537 | A2 | | 9/2006 |
| WO | 2007014051 | A2 | | 2/2007 |
| WO | 2007022518 | A2 | | 2/2007 |
| WO | 2007/055728 | A1 | | 5/2007 |
| WO | 2009064298 | A1 | | 5/2009 |
| WO | 2010/046357 | A1 | | 4/2010 |
| WO | 2010/107874 | A2 | | 9/2010 |
| WO | 2010/139793 | A1 | | 12/2010 |
| WO | 11050008 | A2 | | 4/2011 |
| WO | 12168432 | A1 | | 12/2012 |
| WO | 2012168430 | A2 | | 12/2012 |
| WO | 2012168431 | A2 | | 12/2012 |
| WO | 2013009539 | A1 | | 1/2013 |
| WO | 2013151729 | A1 | | 10/2013 |
| WO | 2013156594 | A1 | | 10/2013 |
| WO | 2013177565 | A1 | | 11/2013 |
| WO | 2014005858 | A1 | | 1/2014 |
| WO | 2014202780 | | | 12/2014 |
| WO | 2017180594 | A1 | | 10/2017 |
| WO | 2017186896 | A1 | | 11/2017 |
| WO | 2019038412 | A1 | | 2/2019 |
| WO | 2019072941 | | | 4/2019 |
| WO | 2019122109 | | | 6/2019 |
| WO | 2020084126 | A1 | | 4/2020 |
| WO | WO2021144476 | | * | 7/2021 |

OTHER PUBLICATIONS

Ozempic, Highlights of Prescribing Information, Dec. 2017, 44 pages.

Liberini et al., "Combined Amylin/GLP-1 pharmacotherapy to promote and sustain long-lasting weight loss", Scientific Reports, Jun. 2019, vol. 9, No. 8447, pp. 1-11.

Sander et al. CAS: 175: 403512, 2021, 2 pages.

Highlights of Prescribing Information for Wegovy approved 2017, published in Jul. 2023, 43 pages.

NCT03600480, "A Research Study of How NNC0174-0833 Taken With Semaglutide Works in People Who are Overweight or Obese", Clinicaltrials.gov, Nov. 2021, 11 pages.

* cited by examiner

PHARMACEUTICAL FORMULATIONS

CROSS-REFERENCE TO RELATED APPLICATIONS

This application is a continuation of U.S. application Ser. No. 17/799,700, filed Aug. 15, 2022, which is a 35 U.S.C. § 371 national stage application of International Application PCT/EP2021/053805, filed Feb. 17, 2021, which claims priority to European Patent Application 20180832.6, filed Jun. 18, 2020, European Patent Application 20180645.2, filed Jun. 17, 2020, European Patent Application 20171240.3, filed Apr. 24, 2020, European Patent Application 20157963.8, filed Feb. 18, 2020, European Patent Application 21154657.7, filed Feb. 2, 2021, European Patent Application 21151004.5, filed Jan. 11, 2021, and European Patent Application 21150056.6, filed Jan. 4, 2021; all of which are hereby incorporated by reference.

TECHNICAL FIELD

The current invention relates to aqueous pharmaceutical formulations of semaglutide and cagrilintide that can be administered using a suitable drug delivery device. When co-administered, semaglutide and cagrilintide, and the pharmaceutical formulations comprising them that are disclosed herein, may be used for the treatment of individuals with medical conditions, such as diabetes and obesity and its associated co-morbidities.

BACKGROUND

Obesity, defined as the abnormal or excessive fat accumulation in the body, is now recognised by the World Health Organization (WHO) as a rapidly developing disorder worldwide. It is a leading risk factor in mortality, as well as in a large number of serious conditions such as type 2 diabetes and cardiovascular diseases.

When diet and exercise alone do not suffice in reducing the body mass index (BMI) to an acceptable level, treatment with active pharmaceutical ingredients such as liraglutide, orlistat and naltrexone-bupropion have been shown to cause weight loss in obese individuals. Nonetheless, in many cases bariatric surgery is necessary. While bariatric surgery is currently the most effective treatment in terms of obtaining long-term weight loss, it is an invasive procedure associated with patient risk and high cost. Therefore, a minimally invasive treatment with an efficacy comparable to bariatric surgery would be a significant improvement in the treatment of obesity.

Semaglutide is a glucagon-like peptide 1 (GLP-1) receptor agonist and is the active pharmaceutical ingredient in a marketed product, Ozempic®. Ozempic® is indicated (i) as an adjunct to diet and exercise to improve glycemic control in adults with type 2 diabetes mellitus and (ii) to reduce the risk of major adverse cardiovascular events in adults with type 2 diabetes mellitus and established cardiovascular disease. Semaglutide was first described in WO2006/097537.

Cagrilintide, also known as AM833, is an amylin receptor agonist first described in WO2012/168432. Cagrilintide monotherapy, for the treatment of obesity, is currently in clinical development.

Nonetheless, there is still a long felt need in the art for a non-invasive treatment of obesity that approaches the efficacy of bariatric surgery.

SUMMARY

Disclosed herein is an aqueous formulation comprising cagrilintide;

a buffer which is: glutamic acid/glutamate, in a concentration of about 2-10 mM;

or lactic acid/lactate, in a concentration of about 2-35 mM; or acetic acid/acetate, in a concentration of about 2-10 mM;

90-99% w/w water; and a pH of 3.5-4.5, preferably about pH 4.0.

Disclosed herein is an aqueous formulation comprising: cagrilintide in a concentration of 0.1-20 mg/ml;

a buffer which is: glutamic acid/glutamate, in a concentration of about 2-10 mM;

or lactic acid/lactate, in a concentration of about 2-35 mM; or acetic acid/acetate, in a concentration of about 2-10 mM; and a pH of 3.5-4.5, such as about pH 4.0.

Disclosed herein is an aqueous formulation comprising: semaglutide;

phosphate, in a concentration of more than 15 mM and less than or equal to 45 mM, such as 16-45 mM, such as 20-45 mM, such as 20-40 mM, such as 25-45 mM, such as 25-40 mM, such as 20-35 mM, such as 20-30 mM, such as 25-35 mM, such as about 30 mM;

90-99% w/w water; and a pH of 7.0-8.0, such as about 7.4.

Disclosed herein is aqueous formulation comprising: semaglutide, in a concentration of 0.1-10 mg/ml;

phosphate, in a concentration of more than 15 mM and less than or equal to 45 mM, such as 16-45 mM, such as 20-45 mM, such as 20-40 mM, such as 25-45 mM, such as 25-40 mM, such as 20-35 mM, such as 25-35 mM, such as about 30 mM; and a pH of 7-8, such as about 7.4.

Disclosed herein is a medical device comprising the above-mentioned pharmaceutical formulation comprising semaglutide in a first chamber and the above-mentioned pharmaceutical formulation comprising cagrilintide in a second chamber.

Disclosed herein is a medical device comprising a single dose of semaglutide in a first chamber and a single dose of cagrilintide in a second chamber.

Disclosed herein is a fixed-dose combination of 0.025-5.0 mg cagrilintide and 0.05-5.0 mg semaglutide for use in medicine.

DESCRIPTION

Figure 1:
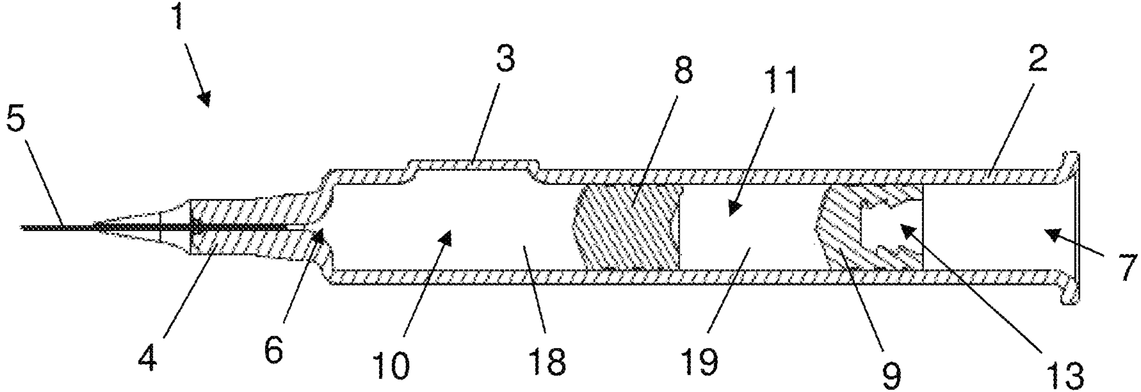
FIG. 1 is a model illustration of a suitable drug delivery device according to an embodiment of the invention. The two liquids are separated by the front (distal) plunger until injection, during which both plungers will be pushed towards the needle. When the front plunger reaches the bypass, the liquid in the rear (proximal) chamber is allowed to flow into the front (distal) chamber.

Disclosed herein is a semaglutide and cagrilintide combination therapy for use in medicine. Studies of such a combination therapy with both semaglutide, a GLP-1 receptor agonist, and cagrilintide, an amylin receptor agonist, have shown a very strong weight-reducing potential, indicating that their co-administration in humans may result in weight loss near to or at the same level as bariatric surgery. This combination therapy may be the answer to the long felt need in the art for a minimally invasive treatment that is on par with bariatric surgery. Furthermore and surprisingly, the combination therapy results in a degree of unwanted side effects, such as gastrointestinal disorders, which is comparable to what is generally seen for GLP-1 receptor agonists alone.

Unfortunately, semaglutide and cagrilintide cannot be formulated in the same pharmaceutical formulation. To ensure chemical as well as physical stability, semaglutide must be formulated at pH 7-8; such as about pH 7.4. To ensure chemical as well as physical stability, cagrilintide must be formulated at pH 3.5-4.5; such as about pH 4.0. The two pharmaceutical formulations comprising semaglutide and cagrilintide, respectively, must be stored separately until they are administered.

However, subcutaneous drug delivery is often associated with discomfort as many people dislike the thought of having an injection needle inserted through the skin. An undisclosed number of people even suffer from needle-phobia. It would be far less uncomfortable and more convenient for these individuals if they only had to inject themselves once, through a single injection needle, to receive the desired combination of semaglutide and cagrilintide: a single, instead of two, injections would result in better adherence to treatment (improved compliance) and, ultimately, improved patient outcome. Furthermore, dosing cagrilintide and semaglutide in a single injection, rather than separately, may influence the efficacy of these active pharmaceutical ingredients.

Dual chamber devices are known in the art, so a first attempt was made to use such a device for the sequential administration of (1) either Ozempic® or a semaglutide pharmaceutical formulation currently in clinical development and (2) the cagrilintide pharmaceutical formulation currently in clinical development.

Ozempic® and the semaglutide pharmaceutical formulation in clinical development are buffered with 8 mM phosphoric acid/phosphate, to keep pH stable at around 7.4. The marketed Ozempic® contains phenol (5.5 mg/ml) as a preservative.

The cagrilintide pharmaceutical formulation used in clinical phase 1 and 2 trials was buffered with 5 mM acetic acid/acetate to keep pH stable at around 4.0. The formulation in clinical phase 1 and 2 trials also contained 20 mM m-cresol as a preservative, 23 mg/ml glycerol as a tonicity agent, HCl/NaOH for pH adjustment and water for injection (WFI).

The inventors of the present invention found that the known semaglutide formulations and the cagrilintide formulation used for phase 1 and 2 (monotherapy) clinical trials could not be stored and administered using a preferred dual-chamber medical device. First of all, the pharmaceutical formulations were not stable during storage in the dual chamber device. Secondly, particles formed when the pharmaceutical formulations were injected through the device.

Disclosed herein are semaglutide and cagrilintide pharmaceutical formulations that are suitable for storage in and administration using a medical device, such as a dual chamber device. Also disclosed herein is a medical device comprising a semaglutide pharmaceutical formulation in one chamber and a cagrilintide pharmaceutical formulation in the other chamber. Disclosed herein is a solution that brings patients closer toward a minimally invasive treatment of obesity that is on par with bariatric surgery.

Cagrilintide

Cagrilintide is an amylin receptor agonist also known as AM833. It is the compound of Example 53 in WO2012/168432: N-alpha-[(S)-4-Carboxy-4-(19-carboxynonadecanoylamino)butyryl]-[Glu14,Arg17,Pro37]-pramlintide. Cagrilintide may be prepared as described in WO2012/168432, pp. 153-155.

In some embodiments cagrilintide is in the form of a salt. In some embodiments, cagrilintide is in the form of a pharmaceutically acceptable salt.

Semaglutide

Semaglutide is a GLP-1 receptor agonist also known as $N^{6.26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid),34-L-arginine]human glucagon-like peptide 1(7-37). Semaglutide, is also described in WHO Drug Information Vol. 24, No. 1, 2010 and may be prepared as described in WO2006/097537, Example 4.

In some embodiments, semaglutide may be present in the composition in its fully or partly ionised form; for example one or more carboxylic acid groups (—COOH) may be deprotonated into the carboxylate group (—COO—) and/or one or more amino groups ($—NH_2$) may be protonated into the $—NH_3^+$ group.

In some embodiments semaglutide is in the form of a salt. In some embodiments, semaglutide is in the form of a pharmaceutically acceptable salt.

Pharmaceutical Formulations

The terms "pharmaceutical formulation", "formulation", "pharmaceutical composition" and "composition" are used interchangeably herein and refer to pharmaceutical formulations suitable for administration to a subject in need thereof. To the person skilled in the art, pharmaceutical formulations and compositions are also known as the "drug product". Disclosed herein are two liquid pharmaceutical formulations that are suitable for parenteral injection, preferably subcutaneous injection. One of the pharmaceutical formulations comprises cagrilintide as the sole active pharmaceutical ingredient. The other pharmaceutical formulation comprises semaglutide as the sole active pharmaceutical ingredient.

Pharmaceutical Formulations Comprising Cagrilintide

Disclosed herein is an aqueous, liquid pharmaceutical formulation comprising cagrilintide as the sole active pharmaceutical ingredient. The cagrilintide formulation disclosed herein has an improved chemical and/or physical stability, compared to known formulations; such as a reduced propensity to form HMWP during storage. The pharmaceutical formulation comprising cagrilintide is suitable for storage in and administration using a suitable medical device, such as a dual chamber device. The composition of the pharmaceutical formulation comprising cagrilintide may be such that cagrilintide is physically and chemically stable during storage in the medical device, whilst in contact with the materials of the chamber in which it is stored. The composition of the pharmaceutical formulation comprising cagrilintide may be such that cagrilintide is physically and chemically stable during ejection from the medical device in which it was stored.

In some embodiments, the pharmaceutical formulation comprising cagrilintide is suitable for storage in, and administration using, a dual chamber device, wherein the latter also contains, in a separate chamber, the pharmaceutical formulation comprising semaglutide that is also disclosed herein.

The pharmaceutical formulation comprising cagrilintide may come into contact with the pharmaceutical formulation comprising semaglutide, as both formulations may, for example, pass through the same device outlet and through the same needle of a dual chamber device. The composition of the pharmaceutical formulation comprising cagrilintide is, preferably, such that it does not have a detrimental effect upon the chemical and/or physical stability of semaglutide during the time that elapses during ejection from the device in which it was stored and injection into a subject.

In some embodiments the pharmaceutical formulation comprises 0.1-20 mg/ml cagrilintide, such as 0.32-18 mg/ml, such as 0.5-18 mg/ml, such as about 1.0 mg/ml, such as about 2.0 mg/ml, such as at least 2 mg/ml, such as about 4.0 mg/ml, such as about 4.8 mg/ml, such as about 6.8 mg/ml, such as about 9.6 mg/ml, such as about 18 mg/ml.

In some embodiments the formulation comprises 1-19 mg/ml cagrilintide. In some embodiments the formulation comprises 2-18 mg/ml cagrilintide. In some embodiments the formulation comprises 3-17 mg/ml cagrilintide. In some embodiments the formulation comprises 4-16 mg/ml cagrilintide. In some embodiments the formulation comprises 5-15 mg/ml cagrilintide. In some embodiments the formulation comprises 6-14 mg/ml cagrilintide. In some embodiments the formulation comprises 7-13 mg/ml cagrilintide. In some embodiments the formulation comprises 8-12 mg/ml cagrilintide. In some embodiments the formulation comprises 9-11 mg/ml cagrilintide. In a preferred embodiment, the formulation comprises 9.6 mg/ml cagrilintide.

In some embodiments, the formulation comprises no more than 20 mg/ml cagrilintide. In some embodiments, the formulation comprises no more than 19 mg/ml cagrilintide. In some embodiments, the formulation comprises no more than 18 mg/ml cagrilintide. In some embodiments, the formulation comprises no more than 17 mg/ml cagrilintide. In some embodiments, the formulation comprises no more than 16 mg/ml cagrilintide. In some embodiments, the formulation comprises no more than 15 mg/ml. In some embodiments, the formulation comprises no more than 14 mg/ml cagrilintide. In some embodiments, the formulation comprises no more than 13 mg/ml cagrilintide. In some embodiments, the formulation comprises no more than 12 mg/ml cagrilintide. In some embodiments, the formulation comprises no more than 11 mg/ml cagrilintide. In some embodiments, the formulation comprises no more than 10 mg/ml cagrilintide. In some embodiments, the formulation comprises no more than 9 mg/ml cagrilintide. In some embodiments, the formulation comprises no more than 8 mg/ml cagrilintide. In some embodiments, the formulation comprises no more than 7 mg/ml cagrilintide. In some embodiments, the formulation comprises no more than 6 mg/ml cagrilintide. In some embodiments, the formulation comprises no more than 5 mg/ml cagrilintide.

In some embodiments, the formulation comprises at least 0.5 mg/ml cagrilintide. In some embodiments, the formulation comprises at least 1 mg/ml cagrilintide. In some embodiments, the formulation comprises at least 2 mg/ml cagrilintide. In some embodiments, the formulation comprises at least 3 mg/ml cagrilintide. In some embodiments, the formulation comprises at least 4 mg/ml cagrilintide. In some embodiments, the formulation comprises at least 5 mg/ml cagrilintide. In some embodiments, the formulation comprises at least 6 mg/ml cagrilintide. In some embodiments, the formulation comprises at least 7 mg/ml cagrilintide. In some embodiments, the formulation comprises at least 8 mg/ml cagrilintide. In some embodiments, the formulation comprises at least 9 mg/ml cagrilintide. In some embodiments, the formulation comprises at least 10 mg/ml cagrilintide. In some embodiments, the formulation comprises at least 11 mg/ml cagrilintide. In some embodiments, the formulation comprises at least 12 mg/ml cagrilintide. In some embodiments, the formulation comprises at least 13 mg/ml cagrilintide. In some embodiments, the formulation comprises at least 14 mg/ml cagrilintide. In some embodiments, the formulation comprises at least 15 mg/ml cagrilintide.

The formulation may comprise one or more pharmaceutically acceptable excipients.

Formulation of cagrilintide at pH 3.5-4.5, such as about pH 4, ensures chemical as well as physical stability of the active pharmaceutical ingredient.

In some embodiments pH is measured at room temperature, such as at 15-25° C. In some embodiments, the formulation comprises a buffer having a pKa close to the desired pH of the solution.

In some embodiments, the buffer in the pharmaceutical formulation comprising cagrilintide is lactate/lactic acid. In some embodiments, the buffer in the pharmaceutical formulation comprising cagrilintide is lactate/lactic acid in a concentration of about 2-35 mM, such as about 2-30 mM, such as 2-25 mM, such as 2-20 mM, such as 2-15 mM, such as 2-10, such as 2.5-10 mM, such as 5-10 mM, such as 2-9 mM, such as 2-8 mM, such as 2-7 mM, such as 2-6 mM, such as about 2.5-5 mM, such as about 5 mM.

In some embodiments, the buffer in the pharmaceutical formulation comprising cagrilintide is glutamate/glutamic acid. In some embodiments, the buffer in the pharmaceutical formulation comprising cagrilintide is glutamate/glutamic acid in a concentration of 2-10 mM, such as 2.5-10 mM, such as 5-10 mM, such as 2-9 mM, such as 2-8 mM, such as 2.5-7.5 mM, such as 2-7 mM, such as 2-6 mM, such as 4-6 mM, such as about 2.5-5 mM, such as about 5 mM.

In some embodiments, the buffer in the pharmaceutical formulation comprising cagrilintide is acetic acid/acetate. In some embodiments, the buffer in the pharmaceutical formulation comprising cagrilintide is acetic acid/acetate in a concentration of about 2-10 mM, such as 2.5-10 mM, such as 2-9 mM, such as 2-8 mM, such as 2-7 mM, such as 2-6 mM, such as about 2.5-5.0 mM, such as about 5 mM.

The concentration of buffer in the pharmaceutical formulation comprising cagrilintide must be high enough to ensure sufficient pH stability around 3.5-4.5, such as about pH 4.0, during storage in the medical device. The concentration of buffer in the pharmaceutical formulation comprising cagrilintide must also be low enough to prevent the pH, during ejection from the device and injection into a subject (and therefore mixing with the pharmaceutical formulation comprising semaglutide), from dropping to a level that causes semaglutide to precipitate or form particles.

The pharmaceutical formulation comprising cagrilintide may further comprise a tonicity agent. The purpose of the tonicity agent may be to protect living tissue when the formulation is injected into the body. For example, the presence of the tonicity agent may be to render the injection relatively painless, or to prevent necrosis. The tonicity agent may be selected from the group consisting of glycerol, mannitol, propylene glycol, sorbitol, sucrose or trehalose. The tonicity agent may be selected from the group consisting of glycerol, mannitol, sorbitol, sucrose or trehalose. In some embodiments, the tonicity agent is glycerol. In some embodiments, the tonicity agent is mannitol. In some embodiments, the tonicity agent is propylene glycol. In some embodiments, the tonicity agent is sorbitol. In some embodiments, the tonicity agent is sucrose. In some embodiments, the tonicity agent is trehalose.

The concentration of the tonicity agent is such as to render the formulation isotonic.

Where the tonicity agent is glycerol, it may be present in a concentration of 20-31 mg/ml, such as about 24 mg/ml.

Where the tonicity agent is mannitol, it may be present in a concentration of 40-60 mg/ml, such as about 46 mg/ml.

Where the tonicity agent is propylene glycol, it may be present in a concentration of 17-26 mg/ml, such as about 20 mg/ml.

Where the tonicity agent is sorbitol, it may be present in a concentration of 40-60 mg/ml, such as about 46 mg/ml.

Where the tonicity agent is sucrose, it may be present in a concentration of 73-105 mg/ml, such as about 83 mg/ml.

Where the tonicity agent is trehalose, it may be present in a concentration of 73-105 mg/ml, such as about 83 mg/ml.

The pharmaceutical formulation may further comprise one or more agents for adjusting pH, such as NaOH and/or HCl.

The pharmaceutical formulation comprises water for injection (WFI). The pharmaceutical formulation may comprise more than 90% w/w water, such as 90-99% w/w water, such as 91-99% w/w water, such as 92-99% w/w water, such as 93-99% w/w water, such as 94-99% w/w water; such as more than 91% w/w water, such as more than 92% w/w water, such as more than 93% w/w water, such as more than 94% w/w water, such as about 95% w/w water, such as more than 95% w/w water, such as about 96% w/w water, such as more than 96% w/w water, such as about 97% w/w water, such as more than 97% w/w water, such as about 98% w/w water, such as more than 98% w/w water.

In some embodiments, the cagrilintide formulation comprises no preservative. In some embodiments, the pharmaceutical formulation comprises no m-cresol.

The cagrilintide formulation disclosed herein is suitable for use in medicine.

The cagrilintide formulation disclosed herein is suitable for parenteral administration, such as subcutaneous administration.

Pharmaceutical Formulations Comprising Semaglutide

Disclosed herein is an aqueous, liquid pharmaceutical formulation comprising semaglutide as the sole active pharmaceutical ingredient. The pharmaceutical formulation comprising semaglutide is suitable for storage in, and administration using, a suitable medical device, such as a dual chamber device. The composition of the pharmaceutical formulation comprising semaglutide is preferably such that semaglutide is physically and chemically stable during storage in the device, whilst in contact with the materials of the chamber in which it is stored. The composition of the semaglutide pharmaceutical formulation is, preferably, such that semaglutide remains chemically and/or physically stable during ejection from the device and injection into a subject.

During parenteral injection, the pharmaceutical formulation comprising semaglutide may come into contact with the pharmaceutical formulation comprising cagrilintide, as both formulations are ejected through the same device outlet/needle of the dual chamber device. The composition of the pharmaceutical formulation comprising semaglutide may be such that it does not have a detrimental effect upon the chemical and/or physical stability of cagrilintide during the time that elapses during ejection from the device and injection into a subject.

Disclosed herein is a liquid pharmaceutical formulation comprising semaglutide, no more than 0.1% (w/w) phenol, sodium chloride and/or potassium chloride.

In some embodiments, the pharmaceutical formulation comprising semaglutide is suitable for storage in, and administration using, a dual-chamber medical device, wherein the latter also contains, in a separate chamber, the pharmaceutical formulation comprising cagrilintide that is disclosed herein.

In some embodiments the formulation comprises 0.1-10 mg/ml semaglutide. In some embodiments the formulation comprises 1-9 mg/ml semaglutide. In some embodiments the formulation comprises 2-8 mg/ml semaglutide. In some embodiments the formulation comprises 3-7 mg/ml semaglutide. In some embodiments the formulation comprises 4-6 mg/ml semaglutide.

In some embodiments the formulation comprises 0.1-5 mg/ml semaglutide. In some embodiments the formulation comprises 0.5-5.0 mg/ml semaglutide. In some embodiments the formulation comprises 4.0-5.5 mg/ml semaglutide. In some embodiments the formulation comprises 4.5-6.0 mg/ml semaglutide. In some embodiments the formulation comprises 4.5-5.0 mg/ml semaglutide.

In preferred embodiments, the formulation comprises about 0.5 mg/ml, about 1.0 mg/ml, about 2.0 mg/ml, about 3.4 mg/ml or about 4.8 mg/ml semaglutide.

In some embodiments the concentration of semaglutide is 0.5-10 mg/ml or 0.01-3.5 mg/ml of said pharmaceutical formulation. In some embodiments the concentration of semaglutide is 0.5 mg/ml, alternatively 1 mg/ml, alternatively 1.5 mg/ml, alternatively 2 mg/ml, alternatively 2.5 mg/ml, alternatively 3 mg/ml, alternatively 3.5 mg/ml.

In some embodiments, the formulation comprises no more than 10 mg/ml semaglutide. In some embodiments, the formulation comprises no more than 9 mg/ml semaglutide. In some embodiments, the formulation comprises no more than 8 mg/ml semaglutide. In some embodiments, the formulation comprises no more than 7 mg/ml semaglutide. In some embodiments, the formulation comprises no more than 6 mg/ml semaglutide. In some embodiments, the formulation comprises no more than 5 mg/ml. In some embodiments, the formulation comprises no more than 4 mg/ml semaglutide. In some embodiments, the formulation comprises no more than 3 mg/ml semaglutide. In some embodiments, the formulation comprises no more than 2 mg/ml semaglutide. In some embodiments, the formulation comprises no more than 1 mg/ml semaglutide.

In some embodiments, the formulation comprises at least 0.5 mg/ml semaglutide. In some embodiments, the formulation comprises at least 1 mg/ml semaglutide. In some embodiments, the formulation comprises at least 2 mg/ml semaglutide. In some embodiments, the formulation comprises at least 3 mg/ml semaglutide. In some embodiments, the formulation comprises at least 4 mg/ml semaglutide. In some embodiments, the formulation comprises at least 5 mg/ml semaglutide. In some embodiments, the formulation comprises at least 6 mg/ml semaglutide. In some embodiments, the formulation comprises at least 7 mg/ml semaglutide. In some embodiments, the formulation comprises at least 8 mg/ml semaglutide. In some embodiments, the formulation comprises at least 9 mg/ml semaglutide.

In a preferred embodiment, the formulation comprises 4.8 mg/ml semaglutide.

The formulation may comprise one or more pharmaceutically acceptable excipients.

Figure 2:
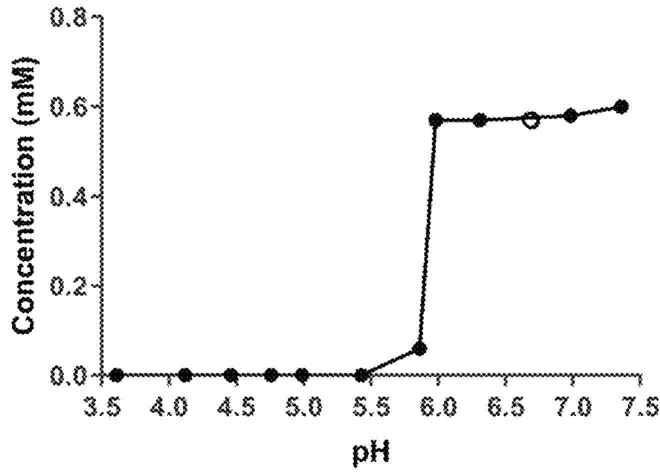
FIG. 2 depicts semaglutide solubility in the pH range 3.5-7.5. Concentrations at or above approximately 0.6 mM (corresponding to approximately 2.5 mg/ml) indicate that all semaglutide added has dissolved, i.e. maximum solubility is above 0.6 mM when the pH is above about 5.9. Concentrations below ca. 0.6 mM indicate that no more than the analysed amount of semaglutide can be dissolved when the pH is below about 5.9.
Figure 3:
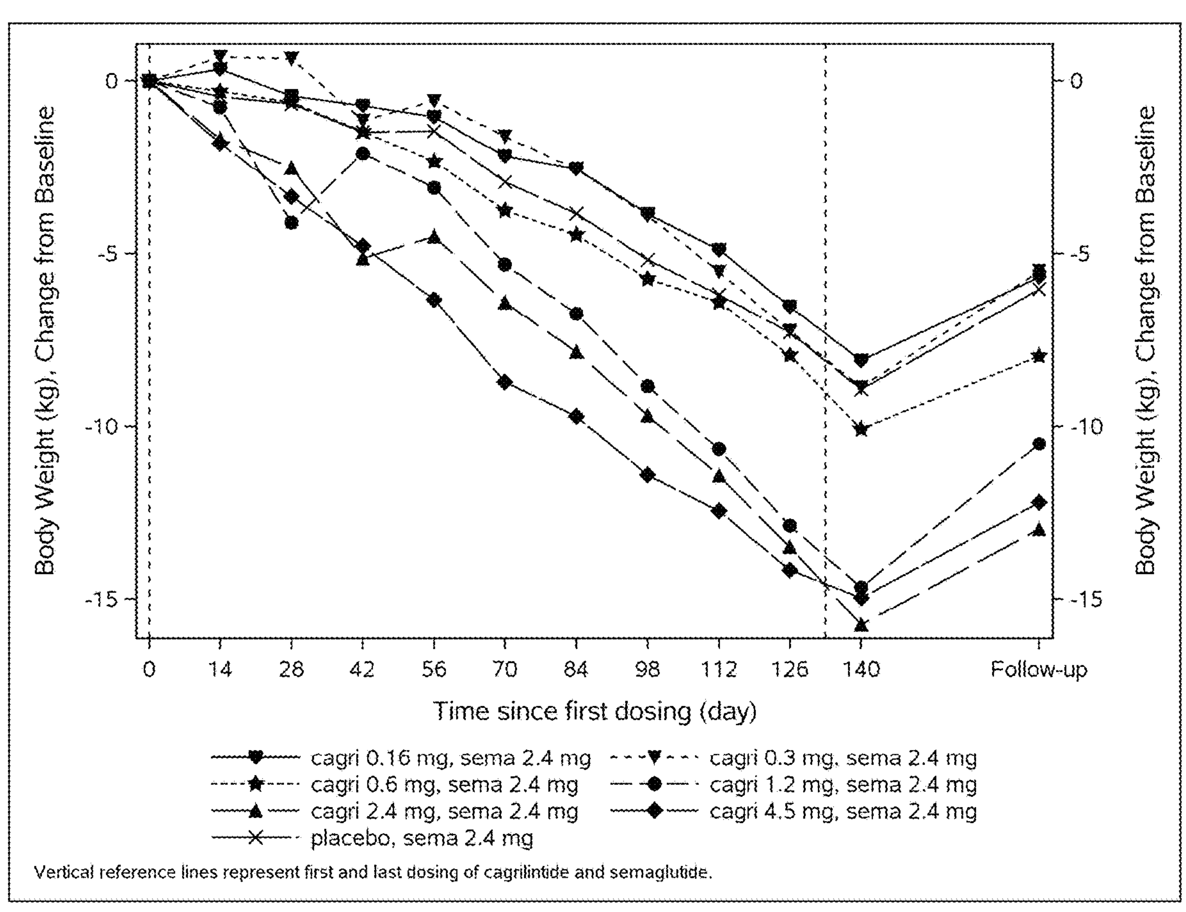
FIG. 3 depicts the weight loss observed in subjects co-dosed with cagrilintide and semaglutide.

The pH of the pharmaceutical formulation comprising semaglutide must be greater than about 5.9 at all times, to ensure that semaglutide remains soluble in water (see FIG. 2). The pH of the pharmaceutical formulation comprising semaglutide must be greater than about 5.9 during storage and during administration.

In some embodiments, the semaglutide formulation has a pH in the range of 6-9. In some embodiments, the semaglutide formulation has a pH in the range of 6.5-8.5. In some embodiments, the semaglutide formulation has a pH in the range of pH 7.0-8.2, such as pH 7.0-8.0, such as pH 7.0-7.8. In some embodiments, the semaglutide formulation has a pH of about 7.4. Formulation of semaglutide at pH 7-8, such as about pH 7.4, ensures chemical as well as physical stability of this active pharmaceutical ingredient.

In some embodiments, pH is measured at room temperature, such as at 15-25° C. In some embodiments, the pharmaceutical formulation comprises a buffer with a pKa close to the desired pH of the solution.

In some embodiments, the buffer is a phosphate buffer. The phosphate buffer may be selected from the group consisting of sodium dihydrogen phosphate, disodium hydrogen phosphate, trisodium phosphate, potassium dihydrogen phosphate, dipotassium hydrogen phosphate and/or tripotassium phosphate.

The concentration of the phosphate buffer may be more than 15 mM and less than or equal to 45 mM, such as 16-45 mM, such as 20-45 mM, such as 20-40 mM, such as 25-45 mM, such as 25-40 mM, such as 20-35 mM, such as 25-35 mM, such as about 30 mM.

In some embodiments, the pharmaceutical formulation comprises a tonicity agent. The purpose of the tonicity agent may be to protect living tissue when the formulation is injected into the body. For example, the presence of the tonicity agent may be to render the injection relatively painless, or to prevent necrosis. The tonicity agent may be selected from the group consisting of propylene glycol, potassium chloride and/or sodium chloride. In some embodiments the formulation comprises a tonicity agent, such as propylene glycol or sodium chloride. In some embodiments the tonicity agent is propylene glycol and/or sodium chloride. In some embodiments, the tonicity agent is not propylene glycol. In some embodiments, the tonicity agent is sodium chloride and/or potassium chloride. In some embodiments, the tonicity agent is sodium chloride.

The concentration of the tonicity agent may be such as to achieve isotonicity in vivo. In a preferred embodiment, the tonicity agent is sodium chloride in a concentration sufficient to achieve isotonicity.

In some embodiments, the tonicity agent is sodium chloride in a concentration of 4.5-8.5 mg/ml, such as 5.0-8.5 mg/ml, such as 5.5-8.5 mg/ml, such as 6.0-8.5 mg/ml, such as 7.0-8.25 mg/ml, such as 4.5-7.0, such as 5.0-7.5 mg/ml, such as 5.0-7.0 mg/ml, such as 5.5-7 mg/ml, such as 6.4-7.9 mg/ml, such as 6.4-7.5 mg/ml, such as 6-7 mg/ml, such as above 6.4 mg/ml, such as about 5.4 mg/ml, such as about 6.4 mg/ml, such as about 6.7 mg/ml.

In some embodiments, the tonicity agent is potassium chloride in a concentration of 5.5-11 mg/ml, such as about 8.2 mg/ml.

In some embodiments the formulation comprises no further tonicity agents.

In some embodiments, the pharmaceutical formulation comprises histidine. In some embodiments the concentration of histidine is 0-20 mM, alternatively 0.5-20 mM, alternatively 0.5-15 mM, alternatively 0.5-10 mM. In some embodiments the concentration of histidine is 1-20 mM, such as 2-20 mM, such as 2-15 mM, such as 2-10 mM, such as 5-20 mM, such as 5-15 mM, such as 5-10 mM, such as 10-20 mM, such as 10-15 mM. In some embodiments the concentration of histidine is 5-15 mM, such as 8-12 mM, such as about 10 mM.

The aqueous semaglutide formulation comprises water for injection (WFI). The semaglutide formulation may comprise more than 60% w/w water, such as more than 90% w/w water, such as 90-99% w/w water, such as 91-99% w/w water, such as 92-99% w/w water, such as 93-99% w/w water, such as 94-99% w/w water, such as 95-99% w/w water, such as 96-99% w/w water, such as 97-99% w/w water, such as 98-99% w/w water; such as at least 91% w/w water, such as at least 92% w/w water, such as at least 93% w/w water, such as at least 94% w/w water, such as about 95% w/w water, such as at least 95% w/w water, such as about 96% w/w water, such as at least 96% w/w water, such as about 97% w/w water, such as at least 97% w/w water, such as about 98% w/w, such as at least 98% w/w water.

The pharmaceutical formulation may further comprise one or more agents for adjusting pH, such as NaOH and/or HCl.

In some embodiments, the pharmaceutical formulation disclosed herein comprises no preservative. In some embodiments the formulation is essentially free of preservative. In some embodiments, the pharmaceutical formulation comprises no phenol.

In some embodiments the pharmaceutical formulation comprises a) semaglutide, such as 0.01-3.5 mg/ml semaglutide or 0.5-10 mg/ml semaglutide, optionally b) no more than 0.1% (w/w) phenol, c) a tonicity agent, d) a buffer, e) at least 60% water, and f) histidine. In some embodiments the tonicity agent is sodium chloride.

In some embodiments the pharmaceutical formulation comprises a) semaglutide, such as 0.01-3.5 mg/ml semaglutide or 0.5-10 mg/ml semaglutide, optionally b) no more than 0.1% (w/w) phenol, c) sodium chloride as a tonicity agent d) buffer, e) at least 60% water, and f) histidine.

In some embodiments the pharmaceutical formulation comprises a) semaglutide, such as 0.01-3.5 mg/ml semaglutide or 0.5-10 mg/ml semaglutide, optionally b) no more than 0.1% (w/w) phenol, c) 2-12 mg/ml sodium chloride, such as 3-12 mg/ml, such as 4-12 mg/I, such as 5-12 mg/ml, such as 6-12 mg/ml sodium chloride d) buffer, e) at least 60% water, and f) histidine.

In some embodiments the pharmaceutical formulation comprises a) semaglutide, such as 0.1-10 mg/ml semaglutide or 0.5-10 mg/ml semaglutide, optionally b) no more than 0.1% (w/w) phenol, c) 5.0-7.0 mg/ml sodium chloride, such as 5.4 or 6.7 mg/ml, d) buffer, e) at least 60% water, and f) histidine.

In some embodiments the pharmaceutical formulation comprises a) semaglutide, such as 0.1-10 mg/ml semaglutide or 0.5-10 mg/ml semaglutide, optionally b) no more than 0.1% (w/w) phenol, c) sodium chloride, d) phosphate, e) water for injection, f) histidine, and optionally NaOH/HCl to reach pH 7-8, such as about pH 7.4.

In some embodiments the pharmaceutical formulation comprises a) semaglutide, such as 0.1-10 mg/ml semaglutide or 0.5-10 mg/ml semaglutide, optionally b) no more than 0.1% (w/w) phenol, c) about or above 6.4 mg/ml sodium chloride, d) buffer, e) at least 60% water, and f) histidine.

In some embodiments the pharmaceutical formulation consists or consists essentially of a) semaglutide, optionally b) no more than 0.1% (w/w) phenol, c) above 6.4 mg/ml sodium chloride, d) buffer, e) at least 60% water, optionally f) histidine, optionally g) one or more agents for adjusting pH, such as HCl, NaOH, or acetate, and said formulation optionally has a pH of 6-10, such as 7-8.

In some embodiments the pharmaceutical formulation consists or consists essentially of a) semaglutide, optionally b) no more than 0.1% (w/w) phenol, c) above 6.4 mg/ml sodium chloride, d) buffer, e) at least 97% water, optionally f) histidine, optionally g) one or more agents for adjusting pH, such as HCl, NaOH, or acetate, and said formulation optionally has a pH of 7-8.

In some embodiments the pharmaceutical formulation consists or consists essentially of a) semaglutide, optionally b) no more than 0.1% (w/w) phenol, c) above 6.4 mg/ml sodium chloride, d) buffer, e) at least 60% water, f) histidine, optionally g) one or more agents for adjusting pH, such as HCl, NaOH, or acetate such as sodium acetate or acetic acid, and said formulation optionally has a pH of 6-10, such as 7-8.

In some embodiments the pharmaceutical formulation consists or consists essentially of a) semaglutide, optionally b) no more than 0.1% (w/w) phenol, c) above 6.4 mg/ml sodium chloride, d) buffer, e) at least 60% water, optionally f) one or more agents for adjusting pH, such as HCl, NaOH, or acetate, and said formulation optionally has a pH of 6-10, such as 7-8.

In some embodiments the pharmaceutical formulation consists or consists essentially of a) semaglutide, optionally b) no more than 0.1% (w/w) phenol, c) above 6.4 mg/ml sodium chloride, d) buffer, e) at least 97% water (such as 97-99%), optionally f) one or more agents for adjusting pH, such as HCl, NaOH, or acetate, and said formulation optionally has a pH of 6-10, such as 7-8.

In some embodiments the semaglutide formulation is for parenteral administration. In some embodiments the semaglutide formulation is for subcutaneous administration.

In some embodiments the semaglutide formulation is for use in an injection device.

Suitable Medical Devices

A medical device may be used for the administration of a predetermined dose of cagrilintide together with a predetermined dose of semaglutide, in a single injection. A medical device may be used for the administration, in a single injection, of a single dose, such as a single effective dose, of cagrilintide together with a single dose, such as a single effective dose, of semaglutide. A medical device may be used for the administration of a cagrilintide pharmaceutical formulation together with a semaglutide pharmaceutical formulation, in a single injection. The medical device may be or comprise a variable volume drug reservoir or a drug delivery device and may comprise a first chamber and a second chamber, which, in a storage, or pre-injection, state of the medical device, are fluidly disconnected. For example, the medical device may be a dual chamber device comprising a tubular wall portion extending along a reference axis, wherein the first chamber and the second chamber are arranged serially along the reference axis. The dual chamber device may extend between a distal end and a proximal end and may further comprise a drug outlet section arranged at the distal end.

A first elastomeric stopper may be arranged in sealing contact with the tubular wall between the drug outlet section and the proximal end to define the first chamber as a distal chamber. A second elastomeric stopper may be arranged in sealing contact with the tubular wall between the first elastomeric stopper and the proximal end to define the second chamber as a proximal chamber.

Based on a desire to enhance user convenience by providing a medical device having small physical dimensions and in view of selected respective concentrations and expected clinically relevant ratios of the cagrilintide pharmaceutical formulation and the semaglutide pharmaceutical formulation, the distal chamber may comprise the semaglutide pharmaceutical formulation and the proximal chamber may comprise the cagrilintide pharmaceutical formulation. From a stability perspective, this specific constellation may further be advantageous when considering the process for filling the two chambers, as the cagrilintide pharmaceutical formulation is more surface reactive than the semaglutide pharmaceutical formulation, and it is difficult to avoid introducing a certain amount of air in the distal chamber by conventional filling methods.

The dual chamber device may further comprise passage means allowing passage of liquid from the proximal chamber to the distal chamber past and/or through the first elastomeric stopper. For example, the tubular wall may comprise a bypass geometry allowing passage of liquid from the proximal chamber to the distal chamber past the first elastomeric stopper when the first elastomeric stopper is in a particular bypass position with respect to the tubular wall. In that case, the first elastomeric stopper is arranged proximally of the bypass geometry in a pre-injection state of the dual chamber device and is adapted to be moved to the bypass position in the cause of a dose administration event.

The drug outlet section may be configured to allow the liquid drug to be expelled through an injection needle, or as a high-pressure jet through a nozzle. In case of the former, an injection needle may be pre-arranged at, e.g. pre-attached to, the drug outlet section, or the drug outlet section may be adapted to receive an injection needle. The drug outlet section may be fluidly sealed, e.g. by a penetrable self-sealing septum.

The dual chamber device may further comprise drug expelling means comprising a piston rod actuatable to apply a driving force to the second elastomeric stopper. The drug expelling means may further comprise energy means such as e.g. a spring member releasable to actuate the piston rod.

In some embodiments, the dual chamber device is a syringe device. In some embodiments, the dual chamber device is a pen injector device. Examples of different dual chamber devices are disclosed in WO 2010/139793, WO 2012/089445 and U.S. Pat. No. 4,394,863.

Alternatively, the medical device may be a dual reservoir device comprising a first reservoir defining the first chamber and a second reservoir defining the second chamber. The first reservoir may comprise a first tubular wall portion extending along a first reference axis, a first drug outlet section and a first elastomeric stopper arranged in sealing contact with the first tubular wall. The second reservoir may comprise a second tubular wall portion extending along a second reference axis, a second drug outlet section and a second elastomeric stopper arranged in sealing contact with the second tubular wall. The first reference axis may be parallel to the second reference axis.

The dual reservoir device may further comprise a needle manifold for allowing fluid transport from the first drug outlet section and the second drug outlet section to a single skin interfacing element.

The needle manifold may comprise a plurality of fluidly interconnected channels comprising a first inlet channel configured for fluid communication with the first drug outlet section, a second inlet channel configured for fluid communication with the second drug outlet section, and an outlet channel in the form of a subcutaneous injection needle.

The dual reservoir device may further comprise drug expelling means for sequential or simultaneous advancement of the first elastomeric stopper within the first tubular wall portion and the second elastomeric stopper within the second tubular wall portion.

Exemplary embodiments of a dual reservoir device are disclosed in WO 2017/114921.

In some embodiments, the tubular wall portion in any one of the devices described above is made of glass. In some embodiments, the tubular wall portion narrows down towards the drug outlet section. In some embodiments, the drug outlet section comprises a wall portion made of glass.

Hence, using a medical device as described above the cagrilintide and semaglutide pharmaceutical formulations are physically separated during storage and are prevented from being mixed until the user initiates a dose administration event and causes an expelling of both pharmaceutical formulations through the single injection needle. The medical device provides convenience to the subject in need of the treatment, thereby encouraging compliance.

For the avoidance of any doubt, in the present context the terms "distal" and "proximal" denote positions at, or directions along, a drug delivery device, a medical reservoir, or a needle unit, where "distal" refers to the drug outlet end and "proximal" refers to the end opposite the drug outlet end. Also, the terms "stopper", "piston" and "plunger" are used interchangeably throughout this document to refer to a movable sealing component in a reservoir body.

FIG. 1 is a longitudinal section view of a drug reservoir 1 according to an exemplary embodiment of the invention. The drug reservoir 1 is depicted in a pre-injection state.

The drug reservoir 1 has a generally cylindrical reservoir body 2 with a bypass channel 3 and a narrowed distal end portion 4. An injection needle 5 is fixed to the distal end portion 4 and establishes fluid communication to a reservoir outlet 6. A front piston 8 is arranged in the reservoir body 2 between the reservoir outlet 6 and an open proximal end 7, and a front chamber 10 is thereby defined by the reservoir outlet 6, a front portion of the reservoir body 2 comprising the bypass channel 3, and the front piston 8. A rear piston 9 is arranged in the reservoir body 2 between the front piston 8 and the open proximal end 7, and a rear chamber 11 is thereby defined by the front piston 8, a middle portion of the reservoir body 2, and the rear piston 9. The rear piston 9 has a cavity 13 adapted to receive an end portion of a piston rod (not shown). Notably, in other exemplary embodiments, the rear piston has no cavity and thereby resembles the front piston. In these embodiments the piston rod is adapted to abut a transversal end surface of the rear piston.

The front chamber 10, which constitutes a distal chamber, holds a neutral or slightly basic liquid pharmaceutical formulation 18 comprising semaglutide, and the rear chamber 11, which constitutes a proximal chamber, holds an acidic liquid pharmaceutical formulation 19 comprising cagrilintide.

In use, when a piston rod is inserted into the cavity 13 and a sufficiently large distally directed force is applied to the rear piston 9 via the piston rod, the rear piston 9 will be set in motion, and due to the incompressibility of the acidic liquid pharmaceutical formulation the force will be transferred on to the front piston 8, which will consequently also be activated. The rear chamber 11 as such is thus displaced within the reservoir body 2, while a volume of the neutral or slightly basic liquid pharmaceutical formulation 18 is forced out through the injection needle 5, until the front piston 8 reaches the bypass channel 3, at which point the acidic liquid pharmaceutical formulation 19 is forced into the bypass channel 3 and past the front piston 8 as the piston rod continues to apply a driving force to the rear piston 9.

The rear chamber 11 eventually collapses as the rear piston 9 approaches the front piston 8 and the acidic liquid pharmaceutical formulation 19 is gradually transferred to the front chamber 10, where it mixes with the remains of the neutral or slightly basic liquid pharmaceutical formulation 18.

Upon complete collapse of the rear chamber 11 the mixture is expelled from the front chamber 10 through the injection needle 5 as the rear piston 9, under the influence of the piston rod, pushes the front piston 8 further distally in the reservoir body 2. The expelling continues until the front piston 8 reaches a constriction of the reservoir body 2 at the reservoir outlet 6.

In a preferred embodiment, the pharmaceutical formulation comprising semaglutide is stored in the distal chamber of the dual chamber device (closest to the needle). The volume of semaglutide pharmaceutical formulation present in the distal chamber may be 400-600 μl, such as about 500-550 μl. The volume of semaglutide pharmaceutical formulation present in the distal chamber may be such as to ensure an extractable volume of about 500 μl.

In some embodiments, the extractable volume of semaglutide pharmaceutical formulation provides a dose of about 0.125 to about 5.0 mg semaglutide. In some embodiments, the extractable volume provides a dose of about 0.125 mg semaglutide. In some embodiments, the extractable volume corresponds to a dose of 0.2-0.3 mg, such as about 0.25 mg semaglutide. In some embodiments, the extractable volume corresponds to a dose of about 0.3 mg semaglutide. In some embodiments, the extractable volume corresponds to a dose of about 0.4 mg semaglutide. In some embodiments, the extractable volume corresponds to a dose of 0.4-0.6 mg, such as about 0.5 mg semaglutide. In some embodiments, the extractable volume corresponds to a dose of about 0.6 mg semaglutide. In some embodiments, the extractable volume corresponds to a dose of about 0.7 mg semaglutide. In some embodiments, the extractable volume corresponds to a dose of about 0.8 mg semaglutide. In some embodiments, the extractable volume corresponds to a dose of about 0.85 mg semaglutide. In some embodiments, the extractable volume corresponds to a dose of about 0.9 mg semaglutide. In some embodiments, the extractable volume corresponds to a dose of 0.9-1.1 mg, such as about 1.0 mg semaglutide. In some embodiments, the extractable volume corresponds to a dose of about 1.1 mg semaglutide. In some embodiments, the extractable volume corresponds to a dose of about 1.2 mg semaglutide. In some embodiments, the extractable volume corresponds to a dose of about 1.3 mg semaglutide. In some embodiments, the extractable volume corresponds to a dose of about 1.4 mg semaglutide. In some embodiments, the extractable volume corresponds to a dose of about 1.5 mg semaglutide. In some embodiments, the extractable volume corresponds to a dose of about 1.6 mg semaglutide. In some embodiments, the extractable volume corresponds to a dose of 1.6-1.8 mg, such as about 1.7 mg semaglutide. In some embodiments, the extractable volume corresponds to a dose of about 1.8 mg semaglutide. In some embodiments, the extractable volume corresponds to a dose of about 1.9 mg semaglutide. In some embodiments, the extractable volume corresponds to a dose of about 2.0 mg semaglutide. In some embodiments, the extractable volume corresponds to a dose of about 2.1 mg semaglutide. In some embodiments, the extractable volume corresponds to a dose of about 2.2 mg semaglutide. In some embodiments, the extractable volume corresponds to a dose of about 2.3 mg semaglutide. In some embodiments, the extractable volume corresponds to a dose of 2.3-2.5 mg, such as about 2.4 mg semaglutide. In some embodiments, the extractable volume corresponds to a dose of about 2.5 mg semaglutide. In some embodiments, the extractable volume corresponds to a dose of about 2.6 mg semaglutide. In some embodiments, the extractable volume corresponds to a dose of about 2.7 mg semaglutide. In some embodiments, the extractable volume corresponds to a dose of about 2.8 mg semaglutide. In some embodiments, the extractable volume corresponds to a dose of about 2.9 mg semaglutide. In some embodiments, the extractable volume corresponds to a dose of about 3.0 mg semaglutide. In some embodiments, the extractable volume corresponds to a dose of about 3.1 mg semaglutide. In some embodiments, the extractable volume corresponds to a dose of about 3.2 mg semaglutide. In some embodiments, the extractable volume corresponds to a dose of about 3.3 mg semaglutide. In some embodiments, the extractable volume corresponds to a dose of about 3.4 mg semaglutide. In some embodiments, the extractable volume corresponds to a dose of about 3.5 mg semaglutide. In some embodiments, the extractable volume corresponds to a dose of about 3.6 mg semaglutide. In some embodiments, the extractable volume corresponds to a dose of about 3.7 mg semaglutide. In some embodiments, the extractable volume corresponds to a dose of about 3.8 mg semaglutide. In some embodiments, the extractable volume corresponds to a dose of about 3.9 mg semaglutide. In some embodiments, the extractable volume corresponds to a dose of about 4.0 mg semaglutide. In some embodiments, the extractable volume corresponds to a dose of about 4.1 mg semaglutide. In some embodiments, the extractable volume corresponds to a dose of about 4.2 mg semaglutide. In some embodiments, the extractable volume corresponds to a dose of about 4.3 mg semaglutide. In some embodiments, the extractable volume corresponds to a dose of about 4.4 mg semaglutide. In some embodiments, the extractable volume corresponds to a dose of about 4.5 mg semaglutide. In some embodiments, the extractable volume corresponds to a dose of about 4.6 mg semaglutide. In some embodiments, the extractable volume corresponds to a dose of about 4.7 mg semaglutide. In some embodiments, the extractable volume corresponds to a dose of about 4.8 mg semaglutide. In some embodiments, the extractable volume corresponds to a dose of about 4.9 mg semaglutide. In some embodiments, the extractable volume corresponds to a dose of about 5.0 mg semaglutide.

In a preferred embodiment, the pharmaceutical formulation comprising cagrilintide is stored in the proximal chamber of the dual chamber device (farthest from the needle). The volume of cagrilintide pharmaceutical formulation present in the proximal chamber may be 200-300 µl, such as 250-300 µl. The volume of cagrilintide pharmaceutical formulation present in the proximal chamber may be such as to ensure an extractable volume of about 250 µl.

In some embodiments, the extractable volume corresponds to a dose of about 0.08 to about 5.0 mg, such as a dose of about 0.125 mg to about 5.0 mg, cagrilintide. In some embodiments, the extractable volume corresponds to a dose of about 0.08 mg cagrilintide. In some embodiments, the extractable volume provides a dose of about 0.125 mg cagrilintide. In some embodiments, the extractable volume corresponds to a dose of about 0.25 mg cagrilintide. In some embodiments, the extractable volume corresponds to a dose of about 0.3 mg cagrilintide. In some embodiments, the extractable volume corresponds to a dose of about 0.4 mg cagrilintide. In some embodiments, the extractable volume corresponds to a dose of about 0.5 mg cagrilintide. In some embodiments, the extractable volume corresponds to a dose of about 0.6 mg cagrilintide. In some embodiments, the extractable volume corresponds to a dose of about 0.7 mg cagrilintide. In some embodiments, the extractable volume corresponds to a dose of about 0.8 mg cagrilintide. In some embodiments, the extractable volume corresponds to a dose of about 0.85 mg cagrilintide. In some embodiments, the extractable volume corresponds to a dose of about 0.9 mg cagrilintide. In some embodiments, the extractable volume corresponds to a dose of about 1.0 mg cagrilintide. In some embodiments, the extractable volume corresponds to a dose of about 1.1 mg cagrilintide. In some embodiments, the extractable volume corresponds to a dose of about 1.2 mg cagrilintide. In some embodiments, the extractable volume corresponds to a dose of about 1.3 mg cagrilintide. In some embodiments, the extractable volume corresponds to a dose of about 1.4 mg cagrilintide. In some embodiments, the extractable volume corresponds to a dose of about 1.5 mg cagrilintide. In some embodiments, the extractable volume corresponds to a dose of about 1.6 mg cagrilintide. In some embodiments, the extractable volume corresponds to a dose of about 1.7 mg cagrilintide. In some embodiments, the extractable volume corresponds to a dose of about 1.8 mg cagrilintide. In some embodiments, the extractable volume corresponds to a dose of about 1.9 mg cagrilintide. In some embodiments, the extractable volume corresponds to a dose of about 2.0 mg cagrilintide. In some embodiments, the extractable volume corresponds to a dose of about 2.1 mg cagrilintide. In some embodiments, the extractable volume corresponds to a dose of about 2.2 mg cagrilintide. In some embodiments, the extractable volume corresponds to a dose of about 2.3 mg cagrilintide. In some embodiments, the extractable volume corresponds to a dose of about 2.4 mg cagrilintide. In some embodiments, the extractable volume corresponds to a dose of about 2.5 mg cagrilintide. In some embodiments, the extractable volume corresponds to a dose of about 2.6 mg cagrilintide. In some embodiments, the extractable volume corresponds to a dose of about 2.7 mg cagrilintide. In some embodiments, the extractable volume corresponds to a dose of about 2.8 mg cagrilintide. In some embodiments, the extractable volume corresponds to a dose of about 2.9 mg cagrilintide. In some embodiments, the extractable volume corresponds to a dose of about 3.0 mg cagrilintide. In some embodiments, the extractable volume corresponds to a dose of about 3.1 mg cagrilintide. In some embodiments, the extractable volume corresponds to a dose of about 3.2 mg cagrilintide. In some embodiments, the extractable volume corresponds to a dose of about 3.3 mg cagrilintide. In some embodiments, the extractable volume corresponds to a dose of about 3.4 mg cagrilintide. In some embodiments, the extractable volume corresponds to a dose of about 3.5 mg cagrilintide. In some embodiments, the extractable volume corresponds to a dose of about 3.6 mg cagrilintide. In some embodiments, the extractable volume corresponds to a dose of about 3.7 mg cagrilintide. In some embodiments, the extractable volume corresponds to a dose of about 3.8 mg cagrilintide. In some embodiments, the extractable volume corresponds to a dose of about 3.9 mg cagrilintide. In some embodiments, the extractable volume corresponds to a dose of about 4.0 mg cagrilintide. In some embodiments, the extractable volume corresponds to a dose of about 4.1 mg cagrilintide. In some embodiments, the extractable volume corresponds to a dose of about 4.2 mg cagrilintide. In some embodiments, the extractable volume corresponds to a dose of about 4.3 mg cagrilintide. In some embodiments, the extractable volume corresponds to a dose of about 4.4 mg cagrilintide. In some embodiments, the extractable volume corresponds to a dose of about 4.5 mg cagrilintide. In some embodiments, the extractable volume corresponds to a dose of about 4.6 mg cagrilintide. In some embodiments, the extractable volume corresponds to a dose of about 4.7 mg cagrilintide. In some embodiments, the extractable volume corresponds to a dose of about 4.8 mg cagrilintide. In some embodiments, the extractable volume corresponds to a dose of about 4.9 mg cagrilintide. In some embodiments, the extractable volume corresponds to a dose of about 5.0 mg cagrilintide.

In some embodiments, the concentration of cagrilintide in the cagrilintide formulation present in one chamber of the device is greater than the concentration of semaglutide in the semaglutide formulation in the other chamber of the device.

Medical Utility

The formulations disclosed herein are for use in medicine.

The aqueous pharmaceutical formulation comprising cagrilintide, disclosed herein, and the aqueous pharmaceutical formulation comprising semaglutide, disclosed herein, are for use in medicine.

Disclosed herein is cagrilintide in combination with semaglutide for use in medicine.

Disclosed herein is a method for the prevention or treatment of a medical disorder or disease, such as diabetes or obesity, wherein cagrilintide in combination with semaglutide are administered to a subject in need thereof.

Disclosed herein is a method for the prevention or treatment of a medical disorder or disease, wherein the liquid pharmaceutical formulations disclosed herein are administered to a subject in need thereof.

The term "treatment", as used herein, refers to the medical therapy of any human or other vertebrate subject in need thereof. Said subject is expected to have undergone physical examination by a medical practitioner, or a veterinary medical practitioner, who has given a tentative or definitive diagnosis which would indicate that the use of said specific treatment is beneficial to the health of said human or other vertebrate. The timing and purpose of said treatment may vary from one individual to another, according to the status quo of the subject's health. Thus, said treatment may be prophylactic (preventative), palliative, symptomatic and/or curative.

Cagrilintide in combination with semaglutide, and/or the cagrilintide and semaglutide formulations disclosed herein, may be used for:

(i) the prevention and/or treatment of all forms of diabetes and associated symptoms, such as hyperglycaemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin-requiring type 2 diabetes, and/or delaying the progression of non-insulin requiring type 2 diabetes to insulin-requiring type 2 diabetes;

(iii) the prevention and/or treatment of eating disorders, such as obesity, e.g. by decreasing food intake, reducing body weight, suppressing appetite, inducing satiety; treating or preventing binge eating disorder, food cravings, bulimia nervosa and/or obesity induced by the administration of an antipsychotic or a steroid; reducing gastric motility; and/or delaying gastric emptying;

(iv) the prevention and/or treatment of cardiovascular disease, such as delaying or reducing the development of a major adverse cardiovascular event (MACE) selected from the group consisting of cardiovascular death, non-fatal myocardial infarction, non-fatal stroke, revascularisation, hospitalisation for unstable angina pectoris, and hospitalisation for heart failure;

(v) the prevention and/or treatment of non-alcoholic fatty liver disease (NAFLD) and/or non-alcoholic steatohepatitis (NASH);

(vi) prevention and/or treatment of cognitive disorders such as Alzheimer's disease.

In some embodiments, the indication is (i). In some embodiments the indication is (ii). In a still further particular aspect the indication is (iii). In a still further particular aspect, the indication is (iv). In a still further particular aspect, the indication is (v). In a still further particular aspect, the indication is (vi). In some embodiments, the indication is type 2 diabetes and/or obesity.

Generally, all subjects suffering from obesity are also considered to be suffering from overweight. Disclosed herein is a method for the treatment or prevention of obesity. Disclosed herein is use of the formulations disclosed herein for the treatment or prevention of obesity. In some embodiments the subject suffering from obesity is human, such as an adult human or a paediatric human (including infants, children, and adolescents).

Body mass index (BMI) is a measure of body fat based on height and weight. The formula for calculation is BMI=weight in kilograms/height in meters$^2$. A human subject suffering from obesity may have a BMI of ≥30; this subject may also be referred to as being obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

Disclosed herein is a method for the treatment or prevention of overweight, optionally in the presence of at least one weight-related comorbidity. Disclosed herein is use of the formulations disclosed herein for the treatment or prevention of overweight, optionally in the presence of at least one weight-related comorbidity.

In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30.

A raised BMI increases the risk of an individual developing any one of a wide range of diseases or co-morbidities. The weight-related comorbidity may be one, or a combination of, the diseases mentioned above. In some embodiments the weight-related comorbidity is selected from the group consisting of hypertension, diabetes (such as type 2 diabetes), dyslipidaemia, high cholesterol and obstructive sleep apnoea.

Disclosed herein is a method for reduction of body weight. A human to be subjected to reduction of body weight may have a BMI of ≥25, such as a BMI of ≥27 or a BMI of ≥30. In some embodiments the human to be subjected to reduction of body weight may have a BMI of ≥35 or a BMI of ≥40. The term "reduction of body weight" may include treatment or prevention of obesity and/or overweight.

In some embodiments, administration of the semaglutide and cagrilintide pharmaceutical formulations disclosed herein may be used as an adjunct to a reduced-calorie diet and increased physical activity for chronic weight management in adult patients with an initial body mass index (BMI) of 30 kg/m2 or greater (obesity) or 27 kg/m2 or greater (overweight) in the presence of at least one weight-related comorbidity (e.g. hypertension, type 2 diabetes mellitus, or dyslipidaemia).

In some embodiments, administration of the semaglutide and cagrilintide pharmaceutical formulations disclose herein may result in >15% weight loss, such as >20% weight loss, such as >25% weight loss, such as >30% weight loss, such as about 15-40% weight loss, such as about 20-35% weight loss, such as about 25-30% weight loss, within 26 weeks of the start of treatment.

In some embodiments, the fixed dose combination of semaglutide and cagrilintide disclosed herein may result in >15% weight loss, such as >20% weight loss, such as >25% weight loss, such as >30% weight loss, such as about 15-40% weight loss, such as about 20-35% weight loss, such as about 25-30% weight loss, within 26 weeks of the start of treatment.

Dosages

As described above, a suitable medical device may be used to administer semaglutide and cagrilintide to an individual in need thereof.

In some embodiments, an effective amount of semaglutide may be administered together with an effective amount of cagrilintide to an individual in need thereof.

In some embodiments, the dose is administered approximately once weekly. In some embodiments, the interval between two fixed doses may be about 4 days, about 5 days, about 6 days, about 7 days, about 8 days, about 9 days or about 10 days. In a preferred embodiment, a fixed maintenance dose is administered approximately once every 7 days (once weekly).

In some embodiments, the dose is administered to individuals having any one of the indications listed above. In some preferred embodiments, the dose is administered to individuals with obesity (body mass index [BMI]≥30 kg/$m^2$). In some preferred embodiments, the dose is administered to individuals that are overweight (BMI≥27 kg/$m^2$-<30 kg/$m^2$) and that have at least one weight-related comorbidity.

In some embodiments, once weekly treatment results in a statistically significant, dose-dependent, reduction in body weight.

Upon initiation of treatment, it may be beneficial to administer ascending doses of cagrilintide and/or semaglutide to individuals in need thereof. Once the individual is acclimatized to the treatment, it may be beneficial to administer maintenance doses of cagrilintide and semaglutide to individuals in need thereof.

In some embodiments, treatment is once weekly and the dose-escalation period is 16 weeks.

In some embodiments, treatment is once weekly and dose escalation is approximately once weekly.

In some embodiments, treatment is once weekly and dose escalation is approximately once every other week.

In some embodiments, treatment is once weekly and dose escalation is approximately once every three weeks.

In some embodiments, treatment is once weekly and dose escalation is approximately once every four weeks.

In some embodiments, ascending doses of cagrilintide are administered together with ascending doses of semaglutide.

In some embodiments, ascending doses of cagrilintide are administered together with a fixed dose of semaglutide.

In some embodiments, ascending doses of cagrilintide are administered together with 2.4 mg semaglutide.

The dose of cagrilintide administered may be 0.025-5.0 mg.

The dose of cagrilintide administered may be 0.08-5.0 mg.

In some embodiments, the dose of cagrilintide administered is 0.08 mg.

In some embodiments, the dose of cagrilintide administered is 0.125 mg.

In some embodiments, the dose of cagrilintide administered is 0.16 mg.

In some embodiments, the dose of cagrilintide administered is 0.25 mg.

In some embodiments, the dose of cagrilintide administered is 0.5 mg.

In some embodiments, the dose of cagrilintide administered is at least 0.6 mg.

In some embodiments, the dose of cagrilintide administered is 0.85 mg.

In some embodiments, the dose of cagrilintide administered is 1.0 mg.

In some embodiments, the dose of cagrilintide administered is 1.1 mg.

In some embodiments, the dose of cagrilintide administered is 1.2 mg.

In some embodiments, the maintenance dose of cagrilintide is 1.2 mg.

In some embodiments, the dose of cagrilintide administered is 1.3 mg.

In some embodiments, the dose of cagrilintide administered is 1.4 mg.

In some embodiments, the dose of cagrilintide administered is 1.5 mg.

In some embodiments, the dose of cagrilintide administered is 1.6 mg.

In some embodiments, the dose of cagrilintide administered is 1.7 mg.

In some embodiments, the dose of cagrilintide administered is 1.8 mg.

In some embodiments, the dose of cagrilintide administered is 1.9 mg.

In some embodiments, the dose of cagrilintide administered is 2.0 mg.

In some embodiments, the dose of cagrilintide administered is 2.1 mg.

In some embodiments, the dose of cagrilintide administered is 2.2 mg.

In some embodiments, the dose of cagrilintide administered is 2.3 mg.

In some embodiments, the dose of cagrilintide administered is 2.4 mg.

In some embodiments, the maintenance dose of cagrilintide is 2.4 mg.

In some embodiments, the dose of cagrilintide administered is 2.5 mg.

In some embodiments, the dose of cagrilintide administered is 2.6 mg.

In some embodiments, the dose of cagrilintide administered is 2.7 mg.

In some embodiments, the dose of cagrilintide administered is 2.8 mg.

In some embodiments, the dose of cagrilintide administered is 2.9 mg.

In some embodiments, the dose of cagrilintide administered is 3.0 mg.

In some embodiments, the dose of cagrilintide administered is 3.1 mg.

In some embodiments, the dose of cagrilintide administered is 3.2 mg.

In some embodiments, the dose of cagrilintide administered is 3.3 mg.

In some embodiments, the dose of cagrilintide administered is 3.4 mg.

In some embodiments, the dose of cagrilintide administered is 3.5 mg.

In some embodiments, the dose of cagrilintide administered is 3.6 mg.

In some embodiments, the dose of cagrilintide administered is 3.7 mg.

In some embodiments, the dose of cagrilintide administered is 3.8 mg.

In some embodiments, the dose of cagrilintide administered is 3.9 mg.

In some embodiments, the dose of cagrilintide administered is 4.0 mg.

In some embodiments, the dose of cagrilintide administered is 4.1 mg.

In some embodiments, the dose of cagrilintide administered is 4.2 mg.

In some embodiments, the dose of cagrilintide administered is 4.3 mg.

In some embodiments, the dose of cagrilintide administered is 4.4 mg.

In some embodiments, the dose of cagrilintide administered is 4.5 mg.

In some embodiments, the maintenance dose of cagrilintide is 4.5 mg.

In some embodiments, the dose of cagrilintide administered is 4.6 mg.

In some embodiments, the dose of cagrilintide administered is 4.7 mg.

In some embodiments, the dose of cagrilintide administered is 4.8 mg.

In some embodiments, the dose of cagrilintide administered is 4.9 mg.

In some embodiments, the dose of cagrilintide administered is 5.0 mg.

The dose of semaglutide administered may be about 0.05-5 mg, such as at least 0.5 mg semaglutide.

The dose of semaglutide administered may be about 0.25-3.0 mg.

In some embodiments, the dose of semaglutide administered is 0.25 mg.

In some embodiments, the dose of semaglutide administered is 0.5 mg.

In some embodiments, the dose of semaglutide administered is at least 0.6 mg.

In some embodiments, the dose of semaglutide administered is 0.85 mg.

In some embodiments, the dose of semaglutide administered is 1.0 mg.

In some embodiments, the dose of semaglutide administered is 1.2 mg.

In some embodiments, the dose of semaglutide administered is 1.5 mg.

In some embodiments, the dose of semaglutide administered is 1.7 mg.

In some embodiments, the dose of semaglutide administered is 2.4 mg.

In some embodiments, the dose of semaglutide administered is 3.0 mg.

In some embodiments, the ratio of cagrilintide to semaglutide that is administered is 1:2.

In some embodiments, the dose of cagrilintide is 0.125 mg and the dose of semaglutide is 0.25 mg.

In some embodiments, the dose of cagrilintide is 0.25 mg and the dose of semaglutide is 0.5 mg.

In some embodiments, the dose of cagrilintide is 0.5 mg and the dose of semaglutide is 1.0 mg.

In some embodiments, the dose of cagrilintide is 0.85 mg and the dose of semaglutide is 1.7 mg.

In some embodiments, the dose of cagrilintide is 1.2 mg and the dose of semaglutide is 2.4 mg.

In some embodiments, the maintenance dose of cagrilintide is 1.2 mg and the maintenance dose of semaglutide is 2.4 mg.

In some embodiments, the ratio of cagrilintide to semaglutide that is administered is 1:1.

In some embodiments, the dose of cagrilintide is 0.25 mg and the dose of semaglutide is 0.25 mg.

In some embodiments, the dose of cagrilintide is 0.5 mg and the dose of semaglutide is 0.5 mg.

In some embodiments, the dose of cagrilintide is 1.0 mg and the dose of semaglutide is 1.0 mg.

In some embodiments, the dose of cagrilintide is 1.7 mg and the dose of semaglutide is 1.7 mg.

In some embodiments, the dose of cagrilintide is 0.16 mg and the dose of semaglutide is 2.4 mg.

In some embodiments, the dose of cagrilintide is 0.3 mg and the dose of semaglutide is 2.4 mg.

In some embodiments, the dose of cagrilintide is 0.6 mg and the dose of semaglutide is 2.4 mg.

In some embodiments, the dose of cagrilintide is 1.2 mg and the dose of semaglutide is 2.4 mg.

In some embodiments, the maintenance dose of cagrilintide is 1.2 mg and the maintenance dose of semaglutide is 2.4 mg.

In some embodiments, the dose of cagrilintide is 2.4 mg and the dose of semaglutide is 2.4 mg.

In some embodiments, the maintenance dose of cagrilintide is 2.4 mg and the maintenance dose of semaglutide is 2.4 mg.

In some embodiments, the dose of cagrilintide is 4.5 mg and the dose of semaglutide is 2.4 mg.

In some embodiments, the maintenance dose of cagrilintide is 4.5 mg and the maintenance dose of semaglutide is 2.4 mg.

In some embodiments, cagrilintide is administered once-weekly at an initial dose of 0.16 mg and then escalated to the subsequent dosing levels of 0.3 mg, 0.6 mg, 1.2 mg and 2.4 mg every other week, until reaching the target/maintenance dose of 2.4 mg once-weekly.

In some embodiments, cagrilintide is administered once-weekly at an initial dose of 0.3 mg and then escalated to the subsequent dosing levels of 0.6 mg, 1.2 mg and 2.4 mg every other week, until reaching the target/maintenance dose of 2.4 mg once-weekly.

In some embodiments, cagrilintide is administered once-weekly at an initial dose of 0.3 mg and then escalated to the subsequent dosing levels of 0.6 mg, 1.2 mg, 2.4 mg and 4.5 mg, until reaching the target/maintenance dose of 4.5 mg once-weekly.

In some embodiments, 0.25 mg cagrilintide is administered once-weekly and escalated every four weeks to the subsequent dosing level of 0.5 mg and then the target/maintenance dose of 1.0 mg once-weekly.

In some embodiments, 0.25 mg cagrilintide is administered once-weekly and escalated every four weeks to the subsequent dosing level of 0.5 mg and then to the target/maintenance dose of 1.2 mg once-weekly.

In some embodiments, 0.25 mg cagrilintide is administered once-weekly and escalated every four weeks to the subsequent dosing levels of 0.5 mg, 1.0 mg and 1.7 mg, until reaching the target/maintenance dose of 2.4 mg once-weekly.

In some embodiments, 0.25 mg semaglutide is administered once-weekly and escalated every four weeks to the subsequent dosing levels of 0.5 mg, 1.0 mg and 1.7 mg, until reaching the target/maintenance dose of 2.4 mg once-weekly.

In some embodiments, 0.25 mg cagrilintide and 0.25 mg semaglutide are administered once a week for four weeks (weeks 0-3) and escalated every four weeks to the subsequent dosing levels of 0.5 mg cagrilintide and 0.5 semaglutide (weeks 4-7), 1.0 mg cagrilintide and 1.0 semaglutide (weeks 8-11) and 1.7 mg cagrilintide and 1.7 mg semaglutide (weeks 12-15), until reaching the target/maintenance dose of 2.4 mg cagrilintide and 2.4 mg semaglutide mg once-weekly (weeks 16 and thereafter).

Herein, specific values given in relation to numbers or intervals may be construed as being the specific value or as being the approximate value (such as plus or minus 10, 15 or 20 percent of the specific value, when amounts can be provided by weight; such as plus or minus 0.4, when pH is measured).

EMBODIMENTS

The following are non-limiting embodiments of the invention:

1. An aqueous cagrilintide formulation comprising:
   cagrilintide;
   a buffer which is: glutamic acid/glutamate, in a concentration of about 2-10 mM;
   or lactic acid/lactate, in a concentration of about 2-35 mM; or acetic acid/acetate, in a concentration of about 2-10 mM;
   90-99% w/w water; and
   a pH of 3.5-4.5, such as about pH 4.0.
2. An aqueous cagrilintide formulation comprising:
   cagrilintide in a concentration of 0.1-20 mg/ml;
   a buffer which is: glutamic acid/glutamate, in a concentration of about 2-10 mM;
   or lactic acid/lactate, in a concentration of about 2-35 mM; or acetic acid/acetate, in a concentration of about 2-10 mM; and
   a pH of 3.5-4.5, such as pH 4.0.
3. The formulation according to any one of the preceding embodiments, which is a pharmaceutical formulation comprising cagrilintide in a concentration of 0.1-20 mg/ml, such as about 1.0 mg/ml, such as about 2.0 mg/ml, such as at least 2 mg/ml, such as about 4.0 mg/ml, such as about 4.8 mg/ml, such as about 6.8 mg/ml, such as about 9.6 mg/ml, such as about 18 mg/ml.
4. The formulation according to any one of the preceding embodiments, which is a pharmaceutical formulation comprising a single dose of cagrilintide.
5. The formulation according to any one of the preceding embodiments, which is a pharmaceutical formulation comprising an effective dose of cagrilintide.
6. An aqueous cagrilintide formulation comprising:
   a single dose of cagrilintide;
   a buffer which is: glutamic acid/glutamate, in a concentration of about 2-10 mM;
   or lactic acid/lactate, in a concentration of about 2-35 mM; or acetic acid/acetate, in a concentration of about 2-10 mM; and
   having a pH of 3.5-4.5, such as about pH 4.0.
7. An aqueous cagrilintide formulation comprising
   a single effective dose of cagrilintide;
   a buffer which is: glutamic acid/glutamate, in a concentration of about 2-10 mM;
   or lactic acid/lactate, in a concentration of about 2-35 mM; or acetic acid/acetate, in a concentration of about 2-10 mM; and
   having a pH of 3.5-4.5, such as about pH 4.0.
8. The formulation according to any one of embodiments 4-7, wherein said dose of cagrilintide is 0.025-5.0 mg, such as 0.08-5.0 mg, such as about 0.125 mg, such as about 0.16 mg, such as about 0.25 mg, such as about 0.5 mg, such as at least about 0.6 mg, such as about 0.85 mg, such as about 1.0 mg, such as about 1.1 mg, such as about 1.2 mg, such as about 1.3 mg, such as about 1.4 mg, such as about 1.5 mg, such as about 1.6 mg, such as about 1.7 mg, such as about 1.8 mg, such as about 1.9 mg, such as about 2.0 mg, such as about 2.1 mg, such as about 2.2 mg, such as about 2.3 mg, such as about 2.4 mg, such as about 2.5 mg, such as about 2.6 mg, such as about 2.7 mg, such as about 2.8 mg, such as about 2.9 mg, such as about 3.0 mg, such as about 3.1 mg, such as about 3.2 mg, such as about 3.3 mg, such as about 3.4 mg, such as about 3.5 mg, such as about 3.6 mg, such as about 3.7 mg, such as about 3.8 mg, such as about 3.9 mg, such as about 4.0 mg, such as about 4.1 mg, such as about 4.2 mg such as about 4.3 mg, such as about 4.4 mg, such as about 4.5 mg, such as about 4.6 mg, such as about 4.7 mg, such as about 4.8 mg, such as about 4.9 mg, such as about 5.0 mg cagrilintide.
9. The cagrilintide formulation according to any one of the preceding embodiments, wherein the buffer is glutamic acid/glutamate in a concentration of 2-10 mM, such as 2.5-10 mM, such as 2.5-5 mM, such as 5-10 mM, such as 2-9 mM, such as 2-8 mM such as 2.5-7.5 mM, such as 2-7 mM, such as 2-6 mM, such as 4-6 mM, such as about 5 mM.
10. The cagrilintide formulation according to any one of embodiments 1-8, wherein the buffer is lactic acid/lactate, in a concentration of about 2-35 mM, such as about 2-30 mM, such as 2-25 mM, such as 2-20 mM, such as 2-15 mM, such as 2-10, such as 2.5-10 mM, such as 5-10 mM, such as 2-9 mM, such as 2-8 mM, such as 2-7 mM, such as 2-6 mM, such as about 2.5-5 mM, such as about 5 mM.
11. The cagrilintide formulation according to any one of embodiments 1-8, wherein the buffer is acetic acid/acetate, in a concentration of about 2-10 mM, such as 2.5-10 mM, such as 5-10 mM, such as 2-9 mM, such as 2-8 mM, such as 2-7 mM, such as 2-6 mM, such as 2.5-5.0 mM, such as about 5 mM.
12. The formulation according to any one of embodiments 1-9, comprising
    cagrilintide in a concentration of 0.1-20 mg/ml, such as 0.32-18 mg/ml, such as 0.5-18 mg/ml, such as about 9.6 mg/ml;
    glutamic acid/glutamate in a concentration of 2-10 mM, such as 2.5-10 mM, such as 2.5-5 mM, such as 5-10 mM, such as 2-9 mM, such as 2-8 mM, such as 2.5-7.5 mM, such as 2-7 mM, such as 2-6 mM, such as 4-6 mM, such as about 2.5-5.0 mM, such as about 5 mM.

13. The formulation according to any one of embodiments 1-8 or 10, comprising
    cagrilintide in a concentration of 0.1-20 mg/ml, such as 0.32-18 mg/ml, such as about 9.6 mg/ml; and
    lactic acid/lactate in a concentration of about 2-35 mM, such as about 2-30 mM such as 2-25 mM, such as 2-20 mM, such as 2-15 mM, such as 2-10 mM, such as 2.5-10 mM, such as 5-10 mM, such as 2-9 mM, such as 2-8 mM, such as 2-7 mM, such as 2-6 mM, such as 2.5-5.0 mM, such as about 5 mM.
14. The formulation according to any one of embodiments 1-8 or 11, comprising
    cagrilintide in a concentration of 0.1-20 mg/ml, such as about 15-20 mg/ml, such as about 18 mg/ml mg/ml,
    acetic acid/acetate in a concentration of about 2-10 mM, such as 2-9 mM, such as 2-8 mM, such as 2-7 mM, such as 2-6 mM, such as about 2.5-5.0 mM.
15. The cagrilintide formulation according to any one of the preceding embodiments, further comprising a tonicity agent.
16. The cagrilintide formulation according to embodiment 15, wherein the tonicity agent is selected from the group consisting of glycerol, mannitol, propylene glycol, sorbitol, sucrose or trehalose.
17. The cagrilintide formulation according to any one of embodiments 15-16, wherein the tonicity agent is selected from the group consisting of glycerol, mannitol, sorbitol, sucrose or trehalose.
18. The cagrilintide formulation according to any one of embodiments 15-17, wherein the concentration of the tonicity agent is such as to achieve isotonicity.
19. The cagrilintide formulation according to any one of embodiments 15-18, wherein the tonicity agent is glycerol.
20. The cagrilintide formulation according to the preceding embodiment, wherein the concentration of glycerol is 20-31 mg/ml, such as about 24 mg/ml.
21. The cagrilintide formulation according to any one of embodiments 15-18, wherein the tonicity agent is mannitol.
22. The cagrilintide formulation according to the preceding embodiment, wherein the concentration of mannitol is 40-60 mg/ml, such as about 46 mg/ml.
23. The cagrilintide formulation according to any one of embodiments 15-18, wherein the tonicity agent is propylene glycol.
24. The cagrilintide formulation according to the preceding embodiment, wherein the concentration of propylene glycol is 17-26 mg/ml, such as about 20 mg/ml.
25. The cagrilintide formulation according to any one of embodiments 15-18, wherein the tonicity agent is sorbitol.
26. The cagrilintide formulation according to the preceding embodiment, wherein the concentration of sorbitol is 40-60 mg/ml, such as about 46 mg/ml.
27. The cagrilintide formulation according to any one of embodiments 15-18, wherein the tonicity agent is sucrose.
28. The cagrilintide formulation according to the preceding embodiment, wherein the concentration of sucrose is 73-105 mg/ml, such as about 83 ml/mg.
29. The cagrilintide formulation according to any one of embodiments 15-18, wherein the tonicity agent is trehalose.
30. The cagrilintide formulation according to the preceding embodiment, wherein the concentration of trehalose is 73-105 mg/ml, such as about 83 mg/ml.
31. The cagrilintide formulation according to any one of the preceding embodiments, comprising more than 90% w/w water, such as 90-99% w/w water, such as 90-99% w/w water, such as 91-99% w/w water, such as 92-99% w/w water, such as 93-99% w/w water, such as 94-99% w/w water; such as more than 91% w/w water, such as more than 92% w/w water, such as more than 93% w/w water, such as more than 94% w/w water, such as about 95% w/w water, such as more than 95% w/w water, such as about 96% w/w water, such as more than 96% w/w water, such as about 97% w/w water, such as more than 97% w/w water, such as about 98% w/w water, such as more than 99% w/w water.
32. The cagrilintide formulation according to any one of the previous embodiments, wherein said formulation comprises one or more agents for adjusting pH, such as HCl and/or NaOH.
33. The formulation according to any one of the previous embodiments, wherein said cagrilintide is in the form of a pharmaceutically acceptable salt.
34. The cagrilintide formulation according to any one of the previous embodiments, wherein fewer impurities are generated during storage.
35. The cagrilintide formulation according to any one of the previous embodiments, wherein an improved chemical stability of the formulation is obtained.
36. The cagrilintide formulation according to any one of the previous embodiments, wherein an improved physical stability of the formulation is obtained.
37. The cagrilintide formulation according to any one of the previous embodiments, wherein an improved chemical and physical stability of the formulation is obtained.
38. The cagrilintide formulation according to any one of the previous embodiments, wherein fewer HMWPs are generated during storage.
39. The cagrilintide formulation according to any one of the previous embodiments for use in an injection device.
40. The cagrilintide formulation according to any one of embodiments 1-38 for use in medicine.
41. The cagrilintide formulation according to any one of embodiments 1-38, which is for parenteral administration.
42. The cagrilintide formulation according to any one of embodiments 1-38, which is for subcutaneous administration.
43. An aqueous semaglutide formulation comprising:
    semaglutide;
    no more than 0.1% (w/w) phenol;
    sodium chloride and/or potassium chloride to achieve isotonicity;
    a buffer; and
    a pH of 7-8.
44. The semaglutide formulation according to the previous embodiment, wherein said buffer is a phosphate buffer.
45. An aqueous semaglutide formulation comprising:
    semaglutide;
    phosphate, in a concentration of more than 15 mM and less than or equal to 45 mM, such as 16-45 mM, such as 20-45 mM, such as 20-40 mM, such as 25-45 mM, such as 25-40 mM, such as 20-35 mM, such as 20-30 mM, such as 25-35 mM, such as about 30 mM;
    90-99% w/w water for injection; and
    a pH of 7.0-8.0, such as about 7.4.

46. An aqueous semaglutide formulation comprising:
semaglutide, in a concentration of 0.1-10 mg/ml;
phosphate, in a concentration of more than 15 mM and less than or equal to 45 mM, such as 16-45 mM, such as 20-45 mM, such as 20-40 mM, such as 25-45 mM, such as 25-40 mM, such as 20-35 mM, such as 20-30 mM, such as 25-35 mM, such as about 30 mM; and
a pH of 7-8, such as about 7.4.
47. The semaglutide formulation according to any one of embodiments 45-46, comprising semaglutide in a concentration of 0.1-10 mg/ml, such as 0.5-10 mg/ml, such as 0.5-5.0 mg/ml, such as 0.5-4.8 mg/ml, such as about 0.5 mg/ml, such as about 1 mg/ml, such as about 2 mg/ml, such as about 3.4 mg/ml, such as about 4.8 mg/ml.
48. The semaglutide formulation according to any one of embodiments 45-47, which is a pharmaceutical formulation comprising a single dose of semaglutide
49. The semaglutide formulation according to any one of embodiments 45-48, which is a pharmaceutical formulation comprising an effective dose of semaglutide.
50. The semaglutide formulation according to any one of embodiments 45-49, wherein said dose of semaglutide is about 0.05-5 mg, such as about 0.125-5.0 mg, such as about 0.25-3.0 mg, such as about 0.125 mg, such as about 0.2-0.3 mg, such as about 0.25 mg, such as about 0.4 mg, such as about 0.5 mg, such as about 0.4-0.6 mg, such as about 0.6 mg, such as about 0.7 mg, such as about 0.8 mg, such as about 8.5 mg, such as about 0.9 mg, such as about 1.0 mg, such as about 1.1 mg, such as about 1.2 mg, such as about 1.3 mg, such as about 1.4 mg, such as about 1.5 mg, such as about 1.6 mg, such as about 1.7 mg, such as about 1.8 mg, such as about 1.9 mg, such as about 2.0 mg, such as about 2.1 mg, such as about 2.2 mg, such as about 2.3 mg, such as about 2.4 mg, such as about 2.5 mg, such as about 2.6 mg, such as about 2.7 mg, such as about 2.8 mg, such as about 2.9 mg, such as about 3.0 mg.
51. The formulation according to any of embodiments 45-50, wherein said semaglutide is in the form of a pharmaceutically acceptable salt.
52. The semaglutide formulation according to any one of embodiments 45-51, wherein said phosphate buffer is selected from the group consisting of sodium dihydrogen phosphate, disodium hydrogen phosphate and trisodium phosphate, potassium dihydrogen phosphate, dipotassium hydrogen phosphate and tripotassium phosphate.
53. The semaglutide formulation according to any one of embodiments 45-52, wherein said phosphate buffer is disodium hydrogen phosphate, dihydrate.
54. The semaglutide formulation according to any one of embodiments 45-53, wherein the concentration of the phosphate buffer is above 15 mM and less than or equal to 45 mM, such as 16-45 mM, such as 20-45 mM, such as 20-40 mM, such as 25-45 mM, such as 25-40 mM, such as 20-35 mM, such as 20-30 mM, such as 25-35 mM, such as about 30 mM.
55. The semaglutide formulation according to any one of embodiments 45-54, further comprising histidine.
56. The semaglutide formulation according to embodiment 55, wherein the concentration of histidine is less than about 20 mM, such as 1-20 mM, such as 5-15 mM, such as 8-12 mM, such as about 10 mM.
57. The semaglutide formulation according to any one embodiments 45-56, further comprising a tonicity agent.
58. The semaglutide formulation according to embodiment 57, wherein the tonicity agent is selected from the group consisting of propylene glycol, potassium chloride and/or sodium chloride.
59. The semaglutide formulation according to any one embodiments 57-58, wherein the tonicity agent is sodium chloride.
60. The semaglutide formulation according to any one embodiments 57-58, wherein the tonicity agent is potassium chloride.
61. The semaglutide formulation according to the preceding embodiment, wherein the tonicity agent is sodium chloride and potassium chloride.
62. The semaglutide formulation according to any one of embodiments 57-61, wherein the concentration of the tonicity agent is such as to achieve isotonicity.
63. The semaglutide pharmaceutical formulation according to any one of embodiments 59, 61 or 62, wherein the concentration of sodium chloride is 4.5-8.5 mg/ml, such as 5.0-8.5 mg/ml, such as 5.5-8.5 mg/ml, such as 6.0-8.5 mg/ml, such as 7.0-8.25 mg/ml, such as 4.5-7.0, such as 5.0-7.5 mg/ml, such as 5.0-7.0 mg/ml, such as 5.5-7 mg/ml, such as 6.4-7.9 mg/ml, such as 6.4-7.5 mg/ml, such as 6-7 mg/ml, such as above 6.4 mg/ml, such as about 5.4 mg/ml, such as about 6.4 mg/ml, such as about 6.7 mg/ml.
64. The semaglutide pharmaceutical formulation according to any one of embodiments 60-62, wherein the concentration of potassium chloride is 5.5-11 mg/ml, such as about 8.2 mg/ml.
65. The semaglutide formulation according to any one of embodiments 45-64, comprising more than 90% w/w water, such as 90-99% w/w water, such as 91-99% w/w water, such as 92-99% w/w water, such as 93-99% w/w water, such as 94-99% w/w water, such as 95-99% w/w water, such as 96-99% w/w water, such as 97-99% w/w water, such as 98-99% w/w water; such as at least 91% w/w water, such as at least 92% w/w water, such as at least 93% w/w water, such as at least 94% w/w water, such as about 95% w/w water, such as at least 95% w/w water, such as about 96% w/w water, such as at least 96% w/w water, such as about 97% w/w water, such as at least 97% w/w water, such as about 98% w/w, such as at least 98% w/w water.
66. The semaglutide formulation according to any one of embodiments 45-65, wherein said formulation comprises one or more agents for adjusting pH, such as HCl or NaOH.
67. The semaglutide formulation according to any one of embodiments 45-66, wherein said formulation comprises no preservative.
68. The semaglutide formulation according to any one of embodiments 45-67, wherein said formulation has a pH of about 7.4.
69. The formulation according to any one of embodiments 45-68, wherein said formulation is for parenteral administration.
70. The semaglutide formulation according to any one of embodiments 45-68, wherein said formulation is for subcutaneous administration.
71. The semaglutide formulation according to any one of embodiments 45-68 for use in an injection device.
72. The semaglutide formulation according to any one of embodiments 45-68, wherein fewer impurities are generated during storage.

73. The semaglutide formulation according to any one of embodiments 45-68, wherein fewer HMWPs are generated during storage.
74. The semaglutide formulation according to any one of embodiments 45-68, wherein an improved chemical stability of the formulation is obtained.
75. The semaglutide formulation according to any one of embodiments 45-68 for use in medicine.
76. The semaglutide formulation according to any one of embodiments 45-68 for use in the treatment and/or prevention of diabetes, obesity, Alzheimer's disease, non-alcoholic fatty liver disease (NAFLD) and/or non-alcoholic steatohepatitis (NASH) and/or cardiovascular diseases.
77. The aqueous pharmaceutical formulation according to any one of embodiments 45-68 for use in the treatment and/or prevention of Alzheimer's disease.
78. The aqueous pharmaceutical formulation according to any one of embodiments 45-68 for use in the treatment and/or prevention of Alzheimer's disease, non-alcoholic fatty liver disease (NAFLD) and/or non-alcoholic steatohepatitis (NASH) and/or cardiovascular diseases.
79. A medical device comprising semaglutide in a first chamber and cagrilintide in a second chamber, such as a single dose of semaglutide in a first chamber and a single dose of cagrilintide in a second chamber.
80. A medical device comprising a first chamber and a second chamber, wherein the first chamber comprises the semaglutide formulation according to any one of embodiments 43-68 and the second chamber comprises the cagrilintide formulation according to any one of embodiments 1-38.
81. The medical device according to any one of embodiments 79-80, further comprising a wall portion extending along a reference axis between a distal end and a proximal end, wherein the first chamber and the second chamber are serially arranged along the reference axis within the wall portion, such that the first chamber constitutes a distal chamber and the second chamber constitutes a proximal chamber.
82. The medical device according to any one of embodiments 80-81, comprising the semaglutide formulation according to any one of embodiments 43-68 in a distal chamber and the cagrilintide formulation according to any one of embodiments 1-38 in a proximal chamber.
83. The medical device according to any one of embodiments 79-82, wherein the cagrilintide formulation comprises lactic acid/lactate, acetic acid/acetate or glutamic acid/glutamate as a buffer (pH 3.5-4.5).
84. The medical device according to any one of embodiments 79-83, wherein the cagrilintide formulation comprises glutamic acid/glutamate as a buffer.
85. The medical device according to embodiment 84, wherein the cagrilintide formulation further comprises
    glycerol, mannitol, propylene glycol, sorbitol, sucrose or trehalose,
    NaOH/HCl to reach pH 3.5-4.5, such as about pH 4.0,
    water.
86. The medical device according to any one of embodiments 79-85, wherein the cagrilintide formulation comprises:
    cagrilintide in a concentration of 0.1-20 mg/ml, such as 0.32-18 mg/ml;
    glutamic acid/glutamate in a concentration of 2-10 mM, such as 2.5-5 mM, such as about 5 mM;
    NaOH/HCl to reach pH 3.5-4.5, such as about pH 4.0;
    water.
87. The medical device according to any one of any one of embodiments 79-83, wherein the formulation comprising cagrilintide further comprises
    lactic acid/lactate,
    glycerol, mannitol, propylene glycol, sorbitol, sucrose or trehalose,
    NaOH/HCl to reach pH 3.5-4.5, such as about pH 4.0,
    water.
88. The medical device according to any one of embodiments 79-83, wherein the formulation comprising cagrilintide comprises:
    cagrilintide in a concentration of 0.1-20 mg/ml, such as 0.32-18 mg/ml,
    lactic acid/lactate, 2.5-10 mM, such as about 5 mM,
    glycerol to obtain isotonicity, such as 24 mg/ml,
    NaOH/HCl to reach pH 3.5-4.5, such as about pH 4.0,
    water.
89. The medical device according to any one of embodiments 79-88, comprising 400-600 μl, preferably about 500-550 μl, of said semaglutide formulation in its distal chamber and 200-300 μl, preferably about 250-300 μl, of said cagrilintide formulation in its proximal chamber.
90. The medical device according to any one of embodiments 79-89, wherein the concentration of cagrilintide in the formulation in the proximal chamber is greater than the concentration of the semaglutide in the formulation in the distal chamber.
91. The medical device according to any one of embodiments 79-90 for use in medicine.
92. The medical device according to any one of embodiments 79-90 for use in the treatment and/or prevention of obesity, diabetes, non-alcoholic fatty liver disease (NAFLD) and/or non-alcoholic steatohepatitis (NASH), cardiovascular diseases and Alzheimer's disease.
93. A medical device comprising a formulation comprising 0.1-10 mg/ml semaglutide in a first chamber and a formulation comprising 0.1-20 mg/ml cagrilintide in a second chamber, for use in the treatment of subjects with an initial body mass index (BMI) of 30 kg/m2 or greater (obesity), or subjects with an initial BMI of 27 kg/m2 or greater (overweight) and at least one weight-related comorbidity.
94. The semaglutide formulation according to any one of embodiments 45-68 and the cagrilintide formulation according to any one of embodiments 1-38 for use in medicine.
95. The semaglutide formulation according to any one of embodiments 45-68 and the cagrilintide formulation according to any one of embodiments 1-38 for use in the treatment and/or prevention of obesity, diabetes, non-alcoholic fatty liver disease (NAFLD) and/or non-alcoholic steatohepatitis (NASH), cardiovascular diseases and/or Alzheimer's disease.
96. The semaglutide formulation according to any one of embodiments 45-68 and the cagrilintide formulation according to any one of embodiments 1-38 for use in the treatment of subjects with an initial body mass index (BMI) of 30 kg/m2 or greater (obesity), or subjects with an initial BMI of 27 kg/m2 or greater (overweight) and at least one weight-related comorbidity.
97. A method for the prevention and/or treatment of obesity, diabetes, non-alcoholic fatty liver disease (NAFLD) and/or non-alcoholic steatohepatitis (NASH), cardiovascular diseases and/or Alzheimer's disease, wherein the semaglutide formulation according to any one of embodiments 45-68 and the cagrilintide formulation according to any one of embodiments 1-38 are administered to a subject in need thereof.

98. A method for the prevention and/or treatment of subjects with an initial body mass index (BMI) of 30 kg/m2 or greater (obesity), or subjects with an initial BMI of 27 kg/m2 or greater (overweight) and at least one weight-related comorbidity, wherein the semaglutide formulation according to any one of the embodiments 45-68 and the cagrilintide formulation according to any one of embodiments 1-38 are administered to a subject in need thereof.

99. An effective, fixed-dose combination of 0.08-5.0 mg cagrilintide and 0.125-5.0 mg semaglutide for use in a method for the treatment of subjects with an initial body mass index (BMI) of 30 kg/m2 or greater (obesity), or subjects with an initial BMI of 27 kg/m2 or greater (overweight) and at least one weight-related comorbidity, wherein the cagrilintide and semaglutide formulations are administered parenterally, such as subcutaneously, in a single injection.

100. The cagrilintide formulation according to any one of embodiments 1-38 and the semaglutide formulation according to any one of embodiments 45-68 for use in a method for the treatment of subjects with subjects with an initial body mass index (BMI) of 30 kg/m2 or greater (obesity), or subjects with an initial BMI of 27 kg/m2 or greater (overweight) and at least one weight-related comorbidity, wherein said cagrilintide and semaglutide formulations are administered parenterally, such as subcutaneously, in a single injection.

101. A formulation comprising 0.1-20 mg/ml cagrilintide and a formulation comprising 0.1-10 mg/ml semaglutide for use in a method for the treatment of subjects with an initial body mass index (BMI) of 30 kg/m2 or greater (obesity), or subjects with an initial BMI of 27 kg/m2 or greater (overweight) and at least one weight-related comorbidity, wherein the cagrilintide and semaglutide formulations are administered parenterally, such as subcutaneously, in a single injection.

102. Use according to any one of embodiments 91-101, wherein the dose of cagrilintide administered in said single injection is from 0.16 mg to 4.5 mg per week, such as about 0.25 mg, 0.5 mg, 1.0 mg, 1.2 mg, 1.7 mg, 2.4 mg or 4.5 mg.

103. Use according to any one of embodiments 91-102, wherein the dose of semaglutide administered in said single injection is about 0.25 mg, 0.5 mg, 1.0 mg, 1.7 mg or 2.4 mg.

104. Use according to any one of embodiments 91-103, wherein the ratio (in mg) of cagrilintide to semaglutide administered is about 1:1.

105. Use according to any one of embodiments 91-103, wherein the ratio (in mg) of cagrilintide to semaglutide administered is about 1:2.

106. Use according to any one of embodiments 91-104, wherein the dose of cagrilintide administered is 0.25 mg and the dose of semaglutide administered is 0.25 mg.

107. Use according to any one of embodiments 91-104, wherein the dose of cagrilintide administered is 0.5 mg and the dose of semaglutide administered is 0.5 mg.

108. Use according to any one of embodiments 91-104, wherein the dose of cagrilintide administered is 1.0 mg and the dose of semaglutide administered is 1.0 mg.

109. Use according to any one of embodiments 91-104, wherein the dose of cagrilintide administered is 1.7 mg and the dose of semaglutide administered is 1.7 mg.

110. Use according to any one of embodiments 91-104, wherein the dose of cagrilintide administered is 2.4 mg and the dose of semaglutide administered is 2.4 mg.

111. Use according to any one of embodiments 91-103 or 105, wherein the dose of cagrilintide administered is 1.2 mg and the dose of semaglutide administered is 2.4 mg.

112. Use according to any one of embodiments 91-111, wherein the cagrilintide and semaglutide formulations are administered, in a single injection, approximately once weekly, such as once every 5-9 days, such as once every 6-8 days, preferably, once every 7 days.

113. Use according to any one of embodiments 91-112, wherein:
    0.25 mg cagrilintide and 0.25 mg semaglutide are administered once a week for four weeks (weeks 0-3); and
    0.5 mg cagrilintide and 0.5 semaglutide are administered once a week for four weeks (weeks 4-7); and
    1.0 mg cagrilintide and 1.0 semaglutide are administered once a week for the four weeks (weeks 8-11); and
    1.7 mg cagrilintide and 1.7 mg semaglutide are administered once a week for the four weeks (weeks 12-15); and
    2.4 mg cagrilintide and 2.4 mg semaglutide mg are administered once a week thereafter.

114. Use according to any one of embodiments 91-113, wherein the fixed dose combination of semaglutide and cagrilintide results in >15% weight loss within 26 weeks of the start of treatment.

EXAMPLES

All compositions of semaglutide drug product (DP) were prepared by dissolving the buffer (disodium hydrogen phosphate, dihydrate), tonicity agent (propylene glycol or NaCl), and histidine (where relevant) in water, and pH was adjusted to approximately 7.4 using sodium hydroxide and/or hydrochloric acid. Semaglutide drug substance (DS) was dissolved therein, pH was adjusted as necessary to 7.4 using sodium hydroxide and/or hydrochloric acid, and the composition was sterilised by filtration through a 0.22 μm sterile filter.

All compositions of cagrilintide drug product (DP) were prepared by dissolving buffer and tonicity agent in water, and pH was adjusted to approximately 7.4 using sodium hydroxide and/or hydrochloric acid. Cagrilintide drug substance (DS) was dissolved therein, pH was adjusted as necessary to 4.0 using sodium hydroxide and/or hydrochloric acid, and the composition was finally sterilised by filtration through a 0.22 μm sterile filter.

Where chlorobutyl rubber plungers are mentioned, the type without a cavity was used, i.e. the geometry was similar to the distal plunger 8 shown in FIG. 1 regardless of whether it served as a distal or proximal plunger.

Example 1: Investigation of Formation Rates of High Molecular Weight Protein (HMWP) Species in Cagrilintide Formulations with Different Buffer Substances or Tonicity Agents An experiment was conducted to determine the optimal buffer substance or substances, as well as the optimal tonicity agent or agents, for the cagrilintide drug product formulation at pH 4.0 with respect to the formation rate of high-molecular weight protein (HMWP) impurities. In general, the level of HMWP in pharmaceutical peptide or protein formulations is an important parameter to consider as part of evaluating the stability of the formulation, and the formation rate of this impurity during storage should be minimised.

The buffer substances investigated were acetate, benzoate, glutamate, and lactate, as these buffers have a $pK_a$ value close to the optimal pH 4.0 of cagrilintide formulations. The tonicity agents investigated were glycerol, mannitol, propylene glycol, sorbitol, sucrose and trehalose.

For the buffer substance investigation, a total of 38 cagrilintide formulations were prepared with the following general composition:

- Cagrilintide in one concentration, as specified in Table 1-1.
- One buffer substance in one concentration, as specified in Table 1-1.
- Tonicity agent: Glycerol (24 mg/ml).
- Hydrochloric acid (HCl), as necessary to obtain pH 4.0.
- Sodium hydroxide (NaOH), as necessary to obtain pH 4.0.
- Water for Injection (WFI) as solvent.

For the tonicity agent investigation, a total of six (6) cagrilintide formulations were prepared, with the following composition:

- Cagrilintide (9.6 mg/ml)
- Buffer substance: Glutamate (5 mM, added as 0.74 mg/ml L-glutamic acid)
- One of the following tonicity agents:
  - Glycerol (24 mg/ml)
  - Mannitol (46 mg/ml)
  - Propylene glycol (20 mg/ml)
  - Sorbitol (46 mg/ml)
  - Sucrose (83 mg/ml)
  - Trehalose (83 mg/ml)
- Hydrochloric acid (HCl), as necessary to obtain pH 4.0
- Sodium hydroxide (NaOH), as necessary to obtain pH 4.0
- Water for Injection (WFI) as solvent.

TABLE 1-1

Overview of cagrilintide formulations included in the buffer substance investigation.

| | Buffer substance and concentration (in mM) | | | | | | | | | | | |
|---|---|---|---|---|---|---|---|---|---|---|---|---|
| | Acetate [1] | | | Benzoate [2] | | | Glutamate [3] | | | Lactate [4] | | |
| | 2.5 | 5 | 10 | 2.5 | 5 | 10 | 2.5 | 5 | 10 | 2.5 | 5 | 10 |
| 0.6 mg/ml cagrilintide | X | X | X | X | X | X | X | X | X | X | X | X |
| 4.0 mg/ml cagrilintide | — | — | — | — | — | — | — | X | — | — | X | — |
| 9.6 mg/ml cagrilintide | X | X | X | X | X | X | X | X | X | X | X | X |
| 18 mg/ml cagrilintide | X | X | X | X | X | X | X | X | X | X | X | X |

(X): The indicated combination of cagrilintide concentration and buffer substance and concentration was included in the study.
(—): The indicated combination of cagrilintide concentration and buffer substance and concentration was not studied.
[1] Added as sodium acetate, trihydrate.
[2] Added as benzoic acid
[3] Added as L-glutamic acid
[4] Added as a 50% w/w sodium L-lactate solution.

Each sterile-filtered formulation was filled in a multitude of glass syringes such that each syringe contained approximately 280 μl of the cagrilintide formulation, enclosed by two chlorobutyl rubber plungers to obtain a configuration of liquid formulation and primary packaging materials corresponding to the proximal chamber of the dual-chamber pre-filled syringe described in the section entitled "Suitable medical devices" and as shown in FIG. 1.

Each syringe was stored at 37±2° C. for 12 weeks, and samples were analysed for content of HMWP at time zero and after 6, 8 and 12 weeks of storage.

The analysis for HMWP is a Size-Exclusion High Performance Liquid Chromatography (SE-HPLC) method, where HMWP species are separated from the main peptide form. The analysis was conducted using a WATERS HMWP, 7.8×300 mm column. Samples formulated to a cagrilintide concentration of 9.6 mg/ml or 18 mg/ml were diluted in a 0.09 M phosphate solution at pH 3.6 to a concentration of 1 mg/ml prior to injection. Samples formulated to a cagrilintide concentration of 0.6 mg/ml were injected as is. The injection volume was 10 μl, and a 500 mM sodium chloride, 10 mM sodium dihydrogen phosphate monohydrate, 5 mM phosphoric acid with 50% (v/v) 2-propanol was used as isocratic eluent. The flow was 0.5 ml/min, and UV detection was obtained at 215 nm wavelength. The content of HMWP (in percent of the total peptide content) is calculated as the HMWP peak area divided by the total area of the HMWP and main peaks, multiplied by 100%.

The rate of formation of HMWP for each of the investigated formulations was calculated as the slope of the linear regression function of the HMWP content (in percent) as a function of time (in weeks).

The results for the buffer substance investigation are presented in Table 1-2.

TABLE 1-2

HMWP formation rates (percent per week) at 37° C. for each buffer substance at each buffer concentration and cagrilintide concentration.

| | Buffer substance and concentration | | | | | |
|---|---|---|---|---|---|---|
| | Acetate | | | Benzoate | | |
| | 2.5 mM | 5 mM | 10 mM | 2.5 mM | 5 mM | 10 mM |
| 0.6 mg/ml cagrilintide | 0.052 | 0.043 | 0.043 | 0.33 | 0.28 | 0.13 |
| 9.6 mg/ml cagrilintide | 0.077 | 0.060 | 0.057 | 0.19 | 0.15 | 0.13 |
| 18 mg/ml cagrilintide | 0.069 | 0.075 | 0.074 | 0.11 | 0.17 | 0.24 |

| | Buffer substance and concentration | | | | | |
|---|---|---|---|---|---|---|
| | Glutamate | | | Lactate | | |
| | 2.5 mM | 5 mM | 10 mM | 2.5 mM | 5 mM | 10 mM |
| 0.6 mg/ml cagrilintide | 0.024 | 0.024 | 0.026 | 0.031 | 0.031 | 0.031 |
| 4.0 mg/ml cagrilintide | — | 0.038 | — | — | 0.041 | — |
| 9.6 mg/ml cagrilintide | 0.057 | 0.045 | 0.045 | 0.063 | 0.047 | 0.048 |
| 18 mg/ml cagrilintide | 0.056 | 0.060 | 0.045 | 0.061 | 0.085 | 0.075 |

(—): Combination not studied.

The following can be observed from results shown in Table 1-2:

In each of the investigated combinations of buffer concentration and cagrilintide concentration, glutamate gave rise to the lowest HMWP formation rates when compared to the other buffer substances.

In each of the investigated combinations of buffer concentration and cagrilintide concentration where benzoate was investigated, benzoate gave rise to the highest HMWP formation rates compared to the other buffer substances.

In each of the investigated combinations of buffer concentration and cagrilintide concentration where all four buffers were investigated, the formulation with acetate or lactate as buffer substance was observed to have a HMWP formation rate closer to that of the formulation with glutamate compared to that of the formulation with benzoate.

In each of the combinations with a cagrilintide concentration up to 9.6 mg/ml where all buffers were investigated, the formulation with lactate exhibited a lower HMWP formation rate compared to that of the corresponding formulation with acetate.

In each of the combinations of a buffer concentration in the range 5-10 mM and a cagrilintide concentration of 18 mg/ml, the formulation with acetate exhibited a lower HMWP formation rate compared to that of the formulation with lactate, whereas in the combination of a buffer concentration of 2.5 mM and a cagrilintide concentration of 18 mg/ml, the formulation with lactate exhibited a lower HMWP formation rate compared to that of the formulation with acetate.

Surprisingly, the data show that choosing glutamate over either acetate, benzoate, or lactate as the buffer substance in the cagrilintide formulation consistently results in the lowest HMWP formation rate, meaning that it results in the most stable cagrilintide formulation based on this parameter.

Further, when the cagrilintide concentration is 9.6 mg/ml and the buffer substance is either glutamate or lactate, the data show that increasing the buffer concentration from 2.5 mM to 5 mM results in a lower HMWP formation rate, however a further increase to 10 mM does not result in a further decrease in HMWP formation rate.

Further, the data surprisingly show that choosing benzoate over either acetate, glutamate, or lactate as the buffering agent in the cagrilintide formulation consistently results in the highest HMWP formation rate, meaning that it results in the least stable cagrilintide formulation based on this parameter.

Further, the data show that choosing lactate as a buffer substance in the concentration range 2.5-5 mM at a cagrilintide concentration of 9.6 mg/ml results in a lower HMWP formation rate compared to the rate if choosing acetate as the buffer substance in the same concentration range, meaning that it results in a more stable cagrilintide formulation based on this parameter.

The results for the investigation with different tonicity agents in a 9.6 mg/ml cagrilintide formulation buffered with 5 mM glutamate are presented in Table 1-3.

TABLE 1-3

| HMWP formation rates (percent per week) at 37° C. for each tonicity agent | | | | | |
|---|---|---|---|---|---|
| Glycerol | Mannitol | Propylene glycol | Sorbitol | Sucrose | Trehalose |
| 0.045 | 0.048 | 0.043 | 0.046 | 0.050 | 0.046 |

The results in Table 1-3 show that glycerol and propylene glycol gave rise to the lowest HMWP formation rates; however the rates are at comparable levels for all six investigated tonicity agents. It can thus be concluded that all six tonicity agents can be used without compromising the stability of the cagrilintide formulation based on this parameter.

Example 2: Investigation of the Physical Stability of Cagrilintide Formulations with Different Buffer Substances Liquid injectable pharmaceutical formulations should remain physically stable throughout the shelf-life of the product, preferably with the possibility to tolerate a period under stressed conditions such as higher temperatures and higher physical stress compared to the recommended long-term storage conditions (typically stored quiescently at 2-8° C.). This will allow patients to carry their medicines with them, e.g. when travelling, thereby increasing both patient safety and patient adherence to the medication.

An experiment was conducted to determine the optimal buffer substance or substances for the cagrilintide drug product formulation at pH 4.0 with respect to the physical stability of the formulation, measured as the development over time of the following parameters:

The amount of sub-visible particles present in the formulation

The presence of amyloid fibrils in the formulation

The amount of sub-visible particles is an important safety parameter to consider in injectable pharmaceutical products, and any development in this parameter for peptide or protein drug products, such as cagrilintide, should be minimised. Cagrilintide is an analogue of the amylin hormone that is known to be able to form amyloid fibrils. The formation of such fibrils should be avoided in parenteral peptide or protein drug products to minimize the risk of immunogenicity reactions in the patient.

The buffer substances investigated were acetate, benzoate, glutamate, and lactate, as these buffers have a $pK_a$ value close to the target pH 4.0 of cagrilintide.

Four (4) cagrilintide formulations were prepared with the following composition, differing only in the buffer substance:

Cagrilintide: 9.6 mg/ml.

One of the following buffer substances in a concentration of 5 mM:
- Acetate (added as sodium acetate, trihydrate)
- Benzoate (added as benzoic acid)
- Glutamate (added as L-glutamic acid
- Lactate (added as a 50% w/w sodium L-lactate solution)

Glycerol: 24 mg/ml

Hydrochloric acid (HCl), as necessary to obtain pH 4.0

Sodium hydroxide (NaOH), as necessary to obtain pH 4.0

Water for Injection (WFI) as solvent.

Each sterile-filtered formulation was filled in a multitude of glass syringes such that each syringe contained approximately 280 μl of the cagrilintide formulation, enclosed by two chlorobutyl rubber plungers to obtain a configuration of liquid formulation and primary packaging materials corresponding to the proximal chamber of the dual-chamber pre-filled syringe described in the section entitled "Suitable medical devices" and as shown in FIG. 1. The plungers were inserted such that approximately 100 μl air was present with the cagrilintide product enclosed by the two plungers.

All syringes were stored at stressed storage conditions, defined in the present experiment as:

Temperature: 37±2° C.

Physical stress: During the storage period, as specified in Table 2-1, all syringes were subject to inversions end-over-end, i.e. 180° inversion back and forth, to allow the product to shift back and forth between the two plungers. The rotations were performed at room temperature at a rate of about 1 second per full inversion (up and down). The frequency and numbers of rotations outlined in Table 2-1 corresponds to an average of 100 full inversions per day, five days per week.

Period: Up to 28 days (see Table 2-2)

TABLE 2-1

Frequency and number of full inversions performed during the study period

| Day no. | No. of full inversions |
|---|---|
| 0 | 100 [A)] |
| 1 | 100 |
| 2 | 100 |
| 3 | 100 |
| 4 | 100 |
| 5 | — |
| 6 | — |
| 7 | 100 |
| 8 | 100 |
| 9 | 100 |
| 10 | 200 |
| 11 | — |
| 12 | — |
| 13 | — |
| 14 | 100 [A)] |
| 15 | 100 |
| 16 | 100 |
| 17 | 200 |
| 18 | — |
| 19 | — |
| 20 | — |
| 21 | 100 [A)] |
| 22 | 100 |
| 23 | 100 |
| 24 | 200 |
| 25 | — |
| 26 | — |
| 27 | — |

(—): No inversion performed.
[A)] Inversions performed after sampling for analysis acc. to Table 2-2.

At the time points indicated in Table 2-2, samples for each of the four cagrilintide formulations were analysed for, Content of sub-visible particles, analysed with micro-flow imaging (MFI)

Presence of amyloid peptide fibrils, analysed with a Thioflavin-T (ThT) fluorescence assay For the analysis for content of sub-visible particles, an MFI method was employed; see e.g. Sharma, D. K. et al. AAPS J. (2010), 12: 455-464 for further details on the principles of the MFI technique. The following procedure was employed for each sample:

The experiment was performed at ambient temperature.

The contents of three syringes was pooled into a sample container.

The liquid from each syringe was taken out by first removing the rear (proximal) plunger by vacuum suction and then pipetting the liquid into the sample container.

The sample was transferred to a 96 deep-well plate which was inserted into the sample handling unit (Bot1) of a Protein Simple MFI™ 5200 apparatus equipped with a standard Protein Simple MFI™ 100 μm flow cell.

The sample was analysed by standard MFI system settings implying that the liquid was pipetted to a reservoir connected to a flow cell, the liquid was illuminated by an LED light source (470 nm), and a digital camera via magnification optics recorded the contents of the flow cell as bright field images throughout the experiment. Data acquisition was accomplished using Protein Simple MVSS software. The recorded image stream from the entire run was processed by validated Novo Nordisk proprietary software MFI Data Validator whereby the number of individual particles of size>2 μm, >5 μm, >10 μm, and >25 μm was obtained (normalised to counts per ml analysed liquid). The particle size is defined as the equivalent circular diameter (ECD).

The analysis for presence of peptide fibrils is based on the fluorescence characteristics of the ThT probe, which displays low fluorescence in the unbound state/native peptide-bound state but high fluorescence when bound to peptide fibrils as well as a red shift in the wavelength of maximum fluorescence upon fibril binding. The following procedure was employed for each sample:

The experiment was performed at 25° C.

The contents of 2 or 3 syringes, as necessary to obtain at least 500 μl in total, was pooled into a sample container.

The liquid from each syringe was taken out by first removing the rear (proximal) plunger by vacuum suction and then pipetting the liquid into the sample container.

Subsequently 500 μl of the sample was mixed with approximately 9 μl a ThT stock solution in a separate sample container, to give a final ThT concentration of 20 μM.

The sample was left to incubate in the dark for 25 min at ambient temperature.

200 μl sample was transferred to a well in a 96-well microtiter plate.

Samples were measured on a BMG CLARIOstar fluorescence plate reader equipped with monochromators for both excitation and emission using 440 nm and 470-550 nm, respectively.

Data acquisition was accomplished using CLARIOstar Control software.

Emission maximum in the present assay was observed to occur at a wavelength of approximately 485 nm; the result for each analysis was therefore reported as the ThT fluorescence at 485 nm, expressed in Relative Fluorescence Units (RFU).

TABLE 2-2

Sampling protocol

| Analysis | 5 mM buffer in the cagrilintide formulation | Time point (days) | | | | | | |
|---|---|---|---|---|---|---|---|---|
| | | 0 | 11 | 14 | 18 | 21 | 25 | 28 |
| Content of sub-visible particles | Acetate | X | X | X | X | — | — | — |
| | Benzoate [A)] | X | X | X | — | — | — | — |
| | Glutamate | X | X | X | X | — | — | — |
| | Lactate | X | X | X | X | — | — | — |

TABLE 2-2-continued

| Sampling protocol | | | | | | | | |
|---|---|---|---|---|---|---|---|---|
| Analysis | 5 mM buffer in the cagrilintide formulation | Time point (days) 0 | 11 | 14 | 18 | 21 | 25 | 28 |
| ThT fluorescence | Acetate | X | X | X | X | X | X | X |
| | Benzoate [A)] | X | X | X | X | X | — | — |
| | Glutamate | X | X | X | X | X | X | X |
| | Lactate | X | X | X | X | X | X | X |

(X): Sampling performed (—): Sampling not performed

[A)] For the benzoate-buffered cagrilintide formulation, sampling was discontinued earlier than for the other formulations because rapid increases in particle content and ThT fluorescence was observed.

The results for content of sub-visible particles at each sampling point analysed with MFI are shown in Table 2-3.

TABLE 2-3

Sub-visible particle counts per ml analysed liquid in cagrilintide formulations with different buffers, as a function of time at stressed storage conditions. Results are divided into the particle size groups, >2 μm, >5 μm, >10 μm, and >25 μm (equivalent circular diameter, ECD) and rounded to nearest integer value.

| | Time point (days 0 | 11 | 14 | 18 |
|---|---|---|---|---|
| 5 mM buffer | Particle size > 2 μm | | | |
| Acetate | 2706 | 7551 | 6973 | 34336 |
| Benzoate | 3802 | 28619 | 64606 | — |
| Glutamate | 1154 | 2748 | 4181 | 12596 |
| Lactate | 1273 | 4475 | 11608 | 25654 |
| | Particle size > 5 μm | | | |
| Acetate | 344 | 1311 | 1858 | 7681 |
| Benzoate | 191 | 7773 | 18886 | — |
| Glutamate | 57 | 650 | 852 | 4326 |
| Lactate | 252 | 879 | 3453 | 6802 |
| | Particle size > 10 μm | | | |
| Acetate | 38 | 103 | 399 | 1513 |
| Benzoate | 11 | 1483 | 3700 | — |
| Glutamate | 4 | 54 | 191 | 971 |
| Lactate | 57 | 23 | 751 | 1586 |
| | Particle size > 25 μm | | | |
| Acetate | 0 | 4 | 134 | 336 |
| Benzoate | 0 | 180 | 432 | — |
| Glutamate | 0 | 0 | 11 | 38 |
| Lactate | 8 | 0 | 31 | 92 |

(—): Not tested, as the experiment was discontinued for enzoate after 14 days.

It can be seen from Table 2-3 that after 14 and 18 days, particle counts at all size intervals are lowest for the glutamate-buffered cagrilintide formulation. Further, up to and including the 14 days' time point the particle counts for the glutamate-buffered cagrilintide formulation remain at low levels, only slightly above the time zero levels; the counts do not appear to accelerate until the 18 days' time point. By comparison, a clear increase in particle counts is observed already at the 11 days' time point for benzoate, or at the 14 days' time point for acetate and lactate.

It is also evident that the particle counts increase most rapidly in the formulation with benzoate as the buffering agent; after 14 days the particle counts were clearly higher for benzoate than after 18 days for any of the other buffers. The sampling for the analysis of sub-visible particle content was discontinued for the benzoate-buffered formulation after 14 days, in part because at that time point the sub-visible particle level had already increased very rapidly (see Table 2-3), and in part because visible particles were detected when inspecting samples from the 18 days' time point visually at approximately 10,000 lux; no visible particles were observed for any of the other buffers throughout the duration of this experiment (up to 28 days when including the part of the study comprising the ThT fluorescence analysis).

After 18 days, the particle counts for acetate and lactate were approximately on par for particle sizes>5 and >10 μm, whereas for >2 and >25 μm the particle counts were higher for acetate compared to lactate.

Based on the sub-visible particle counts it can thus be concluded that,

The cagrilintide formulation buffered with 5 mM glutamate surprisingly retains its physical stability for a longer period at stressed storage conditions compared to acetate, benzoate or lactate.

By a clear margin, the cagrilintide formulation buffered with 5 mM benzoate surprisingly displays the lowest degree of physical stability compared to the other buffers, both by having the fastest onset and the highest levels of sub-visible and visible particle formation The cagrilintide formulations with acetate and lactate display comparable physical stabilities, with lactate providing a slightly more favourable stability compared to acetate.

The results for presence of amyloid fibrils at each sampling point, measured with the ThT fluorescence assay, are shown in Table 2-4.

TABLE 2-4

ThT fluorescence (in RFU) at 485 nm in cagrilintide formulations with different buffers, as a function of time at stressed storage conditions

| 5 mM buffer | Time point (days) 0 | 11 | 14 | 18 | 21 | 25 | 28 |
|---|---|---|---|---|---|---|---|
| Acetate | 639 | 792 | 700 | 819 | 1522 | 2013 | 2749 |
| Benzoate | 811 | 1043 | 3205 | 3161 | 5336 | — | — |
| Glutamate | 574 | 650 | 597 | 634 | 793 | 785 | 816 |
| Lactate | 622 | 685 | 708 | 746 | 858 | 1159 | 1286 |

(—): Not tested, as the experiment was discontinued for benzoate after 21 days.

It can be seen from Table 2-4 that after 28 days at stressed storage conditions the cagrilintide formulation with glutamate retains a level of fluorescence comparable to or slightly above the time zero level. When buffered with lactate, a slightly larger increase is observed after 25 days, reaching a level approximately twice as high at day 28 compared to time zero. A much larger increase in fluorescence is observed for the acetate-buffered formulation, with a rapid increase observed after day 21 and reaching a level after day 28 above four times that observed at time zero. The fastest and largest increase in fluorescence is observed with benzoate as the buffer; a minor increase is observed already after 11 days followed by a large increase after 14 days to a level approximately four times higher than the level at time zero. After another large increase in fluorescence measured at the 21 days' time point, the experiment was discontinued for the benzoate-buffered formulation; visible particles were observed in the samples at this time point when inspected visually under approximately 1,000 lux.

An increase in the ThT fluorescence level, in combination with an increase in the observed amounts of sub-visible particles as detected with the MFI method, indicates that the peptide or protein being investigated is forming amyloid fibrils. Based on the ThT fluorescence results it can thus be concluded that,

- The cagrilintide formulation buffered with glutamate surprisingly remains free or almost free from amyloid fibrils for a longer period at stressed storage conditions compared to acetate, benzoate or lactate, and no or almost no fibrils appear to be forming during the studied period (up to 28 days).
- The cagrilintide formulation buffered with lactate remains free or almost free from amyloid fibrils for a longer period at stressed storage conditions compared to acetate or benzoate, and the levels of fibrils eventually formed during the studied period (observed after 25 days) appear to be lower than with acetate or benzoate when comparing the same time points.
- By a clear margin, the cagrilintide formulation buffered with benzoate surprisingly displays the highest tendency towards forming amyloid fibrils during stressed storage conditions compared to glutamate, lactate and acetate, both in terms of having the fastest onset of formation, and in terms of displaying the largest levels of fibrils.
- The fibrillation tendency of the acetate-buffered formulation during stressed storage conditions appears from the fluorescence levels to fall midway between those of the glutamate-buffered and the benzoate-buffered formulations, both in terms of the time of onset and of the levels of fibrils formed.

In conclusion, 5 mM glutamate surprisingly displays a clear advantage over 5 mM lactate, 5 mM acetate and especially 5 mM benzoate as the buffer with respect to obtaining the most physically stable cagrilintide formulation under stressed storage conditions. Further, both 5 mM lactate and 5 mM acetate each display a clear advantage over 5 mM benzoate as buffers with respect to obtaining the most physically stable cagrilintide formulation under stressed storage conditions.

Example 3: Physical Stability During Injection—the Effect of the Buffer Concentration in Cagrilintide on the Formation of Sub-Visible Particles During Mixing in a Dual-Chamber Syringe The buffer concentration, e.g. the concentration of glutamate or lactate, in the cagrilintide formulation should be sufficiently high to ensure the stability of the cagrilintide drug product during shelf life and out-of-storage, yet upon co-ejection with semaglutide from a dual-chamber syringe it should not compromise the physical stability of semaglutide, e.g. by inducing formation of visible and/or sub-visible particles. Such particle formation could potentially lead to an immunogenic response and/or to an unpredictable pharmaco-kinetic profile in the patient.

An experiment was conducted to determine the maximally feasible concentration of the glutamate or lactate buffer in the cagrilintide formulation at pH 4.0, when considering that mixing with semaglutide should not lead to the formation of visible and/or sub-visible particles.

A total of eight (8) different cagrilintide formulations at pH 4.0 with varying concentrations of glutamate or lactate were prepared, with the following composition:

- Cagrilintide: 9.6 mg/ml
- Glutamate (added as L-glutamic acid) or lactate (added as a 50% w/w sodium L-lactate solution) in one of the following concentrations:
  - 2.5 mM
  - 5 mM
  - 10 mM
  - 40 mM

- Glycerol: 24 mg/ml
- Hydrochloric acid (HCl), as necessary to obtain pH 4.0
- Sodium hydroxide (NaOH), as necessary to obtain pH 4.0
- Water for Injection (WFI) as solvent.

Two (2) semaglutide formulation at pH 7.4, with or without histidine included as an excipient, were prepared with the following composition:

- Semaglutide: 4.8 mg/ml
- Phosphate: 30 mM (added as 5.34 mg/ml disodium hydrogen phosphate, dihydrate)
- Histidine: 0 or 10 mM (added as 1.55 mg/ml L-histidine)
- Sodium chloride: 6.4 mg/ml
- Hydrochloric acid (HCl), as necessary to obtain pH 7.4
- Sodium hydroxide (NaOH), as necessary to obtain pH 7.4
- Water for Injection (WFI) as solvent.

Each sterile-filtered cagrilintide and semaglutide formulation was filled in dual-chamber glass syringes (see FIG. 1) such that each syringe contained approximately 515-525 µl of the semaglutide formulation in the distal chamber towards the needle, and approximately 280 µl of one of the cagrilintide formulations in the proximal chamber enclosed by two chlorobutyl rubber plungers. Thus, a total of twelve different combinations of semaglutide and cagrilintide formulations in dual-chamber syringes were obtained:

- Semaglutide without histidine, paired with each of the cagrilintide formulations with glutamate (four different concentrations)
- Semaglutide with 10 mM histidine, paired with each of the cagrilintide formulations with glutamate (four different concentrations)
- Semaglutide with 10 mM histidine, paired with each of the cagrilintide formulations with lactate (four different concentrations)

In the following, the experiment conducted on one such combination is referred to as an "ejection experiment".

In each ejection experiment, the syringe was emptied by ejecting the entire content of liquid formulation through the needle and into the flow cell of an MFI apparatus. The following procedure was employed for each ejection experiment separately:

- The experiment was performed at ambient temperature.
- The needle tip of the dual-chamber syringe was connected directly to the flow cell (Protein Simple MFI™ 100 µm flow cell) of a Protein Simple MFI™ 4200 apparatus via a silicone tube.
- A force was applied to the rear (proximal) plunger separating the cagrilintide formulation from the external environment, such that an approximately constant flow of liquid of approximately 0.17 ml/min through the flow cell of the MFI apparatus was obtained.
- As the liquid being expelled from the syringe needle passed through the flow cell, the liquid was illuminated by an LED light source (470 nm), and a digital camera via magnification optics recorded the contents of the flow cell as bright field images throughout the experiment. Recording started as soon as possible after the point where all air in the detection zone of the flow cell had been displaced by liquid from the syringe, and ended as close as possible to the point when all liquid contents from the syringe had been expelled and passed through the detection zone of the flow cell. Data acquisition was accomplished using Protein Simple MVSS software.
- The recorded image stream from the entire run was processed by validated Novo Nordisk proprietary software MFI Data Validator whereby the number of individual particles of size>10 µm and size>25 µm (ECD) was obtained (normalised to counts per ml analysed liquid).

The results, given as ranges of particle counts per ml, for each of the investigated semaglutide and cagrilintide combinations are provided in Table 3-1.

TABLE 3-1

| Measured number of particles per ml for each ejection experiment measured with MFI. | | | | |
|---|---|---|---|---|
| Buffer concentration in the cagrilintide | Histidine concentration in the semaglutide | No. of experiments | Number (range) of particles counted, per ml analysed liquid | |
| formulation | formulation | performed (n) | Size > 10 μm | Size > 25 μm |
| 2.5 mM glutamate | 0 mM | 3 | 23-51 | 4-6 |
| 5 mM glutamate | 0 mM | 3 | 23-78 | 0-4 |
| 10 mM glutamate | 0 mM | 1 | 2443 | 103 |
| 40 mM glutamate | 0 mM | 1 | Ca. $2.4 \times 10^{5}$ [A)] | Ca. $4.7 \times 10^{4}$ [A)] |
| 2.5 mM glutamate | 10 mM | 5 | 20-46 | 0 |
| 5 mM glutamate | 10 mM | 5 | 0-22 | 0 |
| 10 mM glutamate | 10 mM | 5 | 257-4306 | 12-227 |
| 40 mM glutamate | 10 mM | — | N/A[B)] | N/A[B)] |
| 2.5 mM lactate | 10 mM | 5 | 2-24 | 0 |
| 5 mM lactate | 10 mM | 5 | 2-156 | 0-4 |
| 10 mM lactate | 10 mM | 5 | 0-24 | 0-4 |
| 40 mM lactate | 10 mM | — | N/A [B)] | N/A [B)] |

[A)] Visible particles were observed to form during ejection, and the very high sub-visible particle counts are therefore associated with uncertainty.
[B)] N/A: Not investigated with MFI. Visible particles were observed to form during ejection, and completing the MFI analysis of sub-visible particle counts is thus not considered relevant; refer also to footnote B above.

To enable comparison with the background particle level of the formulations without mixing taking place, particle counts for the separate formulations, as expelled from syringes in the same manner as the ejection experiments described above, are shown in Table 3-2 (normalised to counts per ml).

TABLE 3-2

| Background particle levels in each formulation (no mixing of cagrilintide and semaglutide) | | |
|---|---|---|
| | Number of particles counted, per ml analysed liquid | |
| Formulation | Size > 10 μm | Size > 25 μm |
| Cagrilintide, 2.5 mM glutamate (n = 2) | 3-8 | 0 |
| Cagrilintide, 5 mM glutamate (n = 2) | 13-16 | 0-2 |
| Cagrilintide, 10 mM glutamate (n = 2) | 3-29 | 0 |
| Cagrilintide, 40 mM glutamate (n = 2) | 18-36 | 0 |
| Cagrilintide, 2.5 mM lactate (n = 2) | 11-18 | 0 |
| Cagrilintide, 5 mM lactate (n = 2) | 3-73 | 0 |
| Cagrilintide, 10 mM lactate (n = 2) | 36-37 | 2 |
| Cagrilintide, 40 mM lactate (n = 2) | 26-34 | 0-2 |
| Semaglutide, 0 mM histidine (n = 2) | 45-64 | 0-27 |
| Semaglutide, 10 mM histidine (n = 2) | 28-209 | 3 |

The MFI particle data show that at glutamate concentrations of 2.5 and 5 mM, the observed particle levels are comparable to the background levels, i.e., no particle formation is observed as a result of mixing with semaglutide. Increasing the glutamate concentration to 10 mM glutamate resulted in increased particle counts for both particle sizes (>10 μm and >25 μm). Increasing the glutamate concentration even further to 40 mM resulted in the formation of visible particles during the ejection experiment, at which point the level of sub-visible particles becomes too high to analyse meaningfully with the MFI apparatus.

For lactate, the MFI particle counts for both particle sizes (>10 μm and >25 μm) remain at low and comparable levels at both 2.5, 5 and 10 mM concentrations, whereas an increase to 40 mM resulted in visible particle formation during the ejection experiment.

Comparing the semaglutide formulations with 0 or 10 mM histidine, the two formulations display comparable particle levels when mixed with each of the four cagrilintide formulations with increasing glutamate concentrations.

The results of this experiment therefore show that,

The glutamate concentration in the cagrilintide formulation at pH 4.0 should not exceed 10 mM, because a glutamate concentration beyond this level could cause excessive formation of sub-visible and, with 40 mM glutamate, even visible particles during co-injection with a semaglutide formulation containing 30 mM phosphate and either 0 or 10 mM histidine at pH 7.4 with the dual-chamber syringe. By contrast, the concentration of glutamate in the cagrilintide formulation at pH 4.0 should be <10 mM, such as 5 mM or 2.5 mM, as this level of glutamate does not cause excessive formation of sub-visible particles during injection using the same combinations.

The lactate concentration in the cagrilintide formulation at pH 4.0 can be up to at least 10 mM, including 2.5 mM or 5 mM, during injection in combination with a semaglutide formulation containing 30 mM phosphate and 10 mM histidine at pH 7.4 with the dual-chamber syringe, as this will not cause formation of sub-visible particles. However, the lactate concentration should not approach 40 mM, as visible particles will form at this concentration.

The results of this physical stability study indicate that 4.8 mg/ml semaglutide formulation containing 30 mM phosphate can optionally contain 10 mM histidine as an excipient; the physical stability of semaglutide and cagrilintide co-injected with the dual-chamber syringe is comparable between the semaglutide formulations with 0 or 10 mM histidine.

Example 4: Physical Stability During Injection—the Effect of Cagrilintide on the Formation of Sub-Visible Particles During Mixing in a Dual-Chamber Syringe In Example 3 it was found that if the concentration of the buffer agent used in the cagrilintide formulation (e.g., glutamate) was increased above a certain threshold, sub-visible or even visible particles would form during co-ejection from dual-chamber syringes with a formulation containing semaglutide. The cagrilintide peptide itself also contributes to the buffer capacity of the cagrilintide formulation; i.e., increasing the cagrilintide concentration leads to an increased buffer concentration.

An experiment was conducted with the dual-chamber syringe to determine whether the presence of the cagrilintide peptide in the cagrilintide formulation (at pH 4.0) would lead to a higher or lower risk of the formation of sub-visible particles during co-ejection from dual-chamber syringes with a semaglutide formulation (at pH 7.4).

A total of three (3) different cagrilintide formulations at pH 4.0 with varying concentrations of cagrilintide were prepared, with the following composition:

Cagrilintide: 0, 0.5, or 9.6 mg/ml
Glutamate: 5 mM (added as 0.74 mg/ml L-glutamic acid)
Glycerol: 24 mg/ml
Hydrochloric acid (HCl), as necessary to obtain pH 4.0
Sodium hydroxide (NaOH), as necessary to obtain pH 4.0
Water for Injection (WFI) as solvent.

Two (2) semaglutide formulation at pH 7.4 were prepared with the following composition:

Semaglutide: 0.5 or 4.8 mg/ml
Phosphate: 30 mM (added as 5.34 mg/ml disodium hydrogen phosphate, dihydrate)
Histidine: 10 mM (added as 1.55 mg/ml L-histidine)
Sodium chloride: 6.4 mg/ml
Hydrochloric acid (HCl), as necessary to obtain pH 7.4
Sodium hydroxide (NaOH), as necessary to obtain pH 7.4
Water for Injection (WFI) as solvent.

Each sterile-filtered cagrilintide and semaglutide formulation was filled in dual-chamber glass syringes (see FIG. 1) such that each syringe contained approximately 520-530 μl of the semaglutide formulation in the distal chamber towards the needle, and approximately 270-280 μl of one of the cagrilintide formulations in the proximal chamber enclosed by two chlorobutyl rubber plungers. Thus, a total of four different combinations of semaglutide and cagrilintide formulations in dual-chamber syringes were obtained (defined as the test combinations):

Semaglutide 0.5 mg/ml paired with cagrilintide 0 mg/ml
Semaglutide 0.5 mg/ml paired with cagrilintide 0.5 mg/ml
Semaglutide 4.8 mg/ml paired with cagrilintide 0 mg/ml
Semaglutide 4.8 mg/ml paired with cagrilintide 9.6 mg/ml In addition, a semaglutide formulation with 0 mg/ml semaglutide was prepared, i.e., a semaglutide vehicle with a composition and pH identical to that stated above for the 0.5 mg/ml and 4.8 mg/ml semaglutide formulations but without semaglutide added to the formulation. This vehicle was used to obtain information on the expected background particle level via the following three combinations (defined as the background combinations):

Semaglutide 4.8 mg/ml in the distal chamber, combined with semaglutide vehicle in the proximal chamber
Semaglutide vehicle in the distal chamber, combined with cagrilintide 0.5 mg/ml in the proximal chamber
Semaglutide vehicle in the distal chamber, combined with cagrilintide 9.6 mg/ml in the proximal chamber For each of the test and background combinations listed above, the "ejection experiment" described in detail in Example 3 was performed, and the number of individual particles of size >10 μm and size >25 μm (ECD) was obtained with the MFI equipment and software (normalised to counts per ml analysed liquid).

The results, given as ranges of particle counts per ml, for each of the four investigated test combinations with semaglutide and cagrilintide formulations are provided in Table 4-1.

TABLE 4-1

Measured number of particles per ml for each ejection experiment performed on the test combinations, measured with MFI.

| Cagrilintide concentration (proximal chamber) | Semaglutide concentration (distal chamber) | No. of experiments performed (n) | Number (range) of particles counted, per ml analysed liquid | |
|---|---|---|---|---|
| | | | Size > 10 μm | Size > 25 μm |
| 0 mg/ml | 0.5 mg/ml | 10 | 0-882 | 0-2 |
| 0.5 mg/ml | 0.5 mg/ml | 9 | 0-30 | 0-7 |
| 0 mg/ml | 4.8 mg/ml | 4 | 215 to ca. $1.7 \times 10^{4}$ [A)] | 19-1563 [A)] |
| 9.6 mg/ml | 4.8 mg/ml | 10 | 0-71 | 0 |

[A)] Visible particles were observed to form in some instances during ejection, and the very high sub-visible particle counts are therefore associated with uncertainty.

Particle counts for the background combinations, as expelled from syringes in the same manner as for the combinations described above, are shown in Table 4-2 (normalised to counts per ml).

TABLE 4-2

Measured number of particles per ml for each ejection experiment performed on the background combinations, measured with MFI.

| Formulation in proximal chamber | Formulation in distal chamber | No. of experiments performed (n) | Number (range) of particles counted, per ml analysed liquid | |
|---|---|---|---|---|
| | | | Size > 10 μm | Size > 25 μm |
| Cagrilintide 0.5 mg/ml | Semaglutide vehicle | 10 | 2-72 | 0 |
| Cagrilintide 9.6 mg/ml | Semaglutide vehicle | 10 | 4-66 | 0-4 |
| Semaglutide vehicle | Semaglutide 4.8 mg/ml | 10 | 14-95 | 0-6 |

The data in Table 4-1 for the test combinations show that the sub-visible particle level for the combination of cagrilintide 0 mg/ml and semaglutide 4.8 mg/ml is clearly elevated compared to the background levels shown in Table 4-2; in some instances even visible particles were observed to form to during ejection. For the combination of cagrilintide 0 mg/ml and semaglutide 0.5 mg/ml, the >10 μm particle level is elevated in some experiments compared to the background levels (see Table 4-2). For the remaining two test combinations, in which cagrilintide was present at concentrations of either 0.5 mg/ml or 9.6 mg/ml, no sub-visible particle formation was observed beyond what could be expected from the background level.

This experiment surprisingly shows that cagrilintide is required to be present at a certain concentration above 0 mg/ml in order to consistently avoid the formation of sub-visible and, in combination with semaglutide 4.8 mg/ml, even visible particles when co-ejecting the tested cagrilintide formulation with the tested semaglutide formulation from the dual-chamber syringe. It is unexpected that the presence of cagrilintide prevents particle formation due to semaglutide precipitation because the cagrilintide peptide contributes to the buffer capacity in the cagrilintide formulation at pH 4.0; the results from Example 3 show that increasing the buffer capacity in the cagrilintide formulation increases the risk of particle formation during mixing of the same cagrilintide and semaglutide formulations that were tested in the present example.

Example 5: Physical Stability During Injection with Varying Phosphate Concentrations in a Semaglutide Formulation The phosphate buffer concentration in the semaglutide formulation should ensure the stability of the semaglutide drug product during shelf life and out-of-storage, as well as the physical stability of semaglutide upon co-ejection with cagrilintide from the dual-chamber device, e.g. by ensuring that visible and/or sub-visible particles do not form. Such particle formation could potentially lead to an immunogenic response and/or to an unpredictable pharmaco-kinetic profile in the patient. In Example 3, the influence of the buffer concentration in the cagrilintide formulation was demonstrated to be of importance with respect to ensuring the physical stability upon co-ejection with semaglutide from the dual-chamber device.

An experiment was conducted to determine the minimum feasible concentration of the phosphate buffer in the semaglutide formulation at pH 7.4, when considering that mixing with cagrilintide should not lead to the formation of visible and/or sub-visible particles.

A total of four (4) semaglutide formulations at pH 7.4 were prepared with varying concentrations of phosphate, with the following composition:

Semaglutide: 4.8 mg/ml

One of the following combinations of phosphate (buffer) and either propylene glycol or sodium chloride as tonicity agent (the concentration of the tonicity agent was adjusted based on the concentration of phosphate to obtain approximately isotonic formulations):

- 8 mM phosphate (added as 1.42 mg/ml disodium hydrogen phosphate, dihydrate) and 18.5 mg/ml propylene glycol
- 15 mM phosphate (added as 2.67 mg/ml disodium hydrogen phosphate, dihydrate) and 17.5 mg/ml propylene glycol
- 20 mM phosphate (added as 3.56 mg/ml disodium hydrogen phosphate, dihydrate) and 17.0 mg/ml propylene glycol
- 20 mM phosphate (added as 3.56 mg/ml disodium hydrogen phosphate, dihydrate) and 7.60 mg/ml sodium chloride Hydrochloric acid (HCl), as necessary to obtain pH 7.4

Sodium hydroxide (NaOH), as necessary to obtain pH 7.4

Water for Injection (WFI) as solvent.

One (1) cagrilintide formulation at pH 4.0 was prepared, with the following composition:

Cagrilintide: 9.6 mg/ml

Glutamate: 5 mM (added as 0.74 mg/ml L-glutamic acid)

Glycerol: 24 mg/ml

Hydrochloric acid (HCl), as necessary to obtain pH 4.0

Sodium hydroxide (NaOH), as necessary to obtain pH 4.0

Water for Injection (WFI) as solvent.

Each sterile-filtered cagrilintide and semaglutide formulation was filled in dual-chamber glass syringes (see FIG. 1) such that each syringe contained an extractable volume of at least 500 μl of one of the semaglutide formulations in the distal chamber towards the needle, and an extractable volume of at least 250 μl of the cagrilintide formulation in the proximal chamber enclosed by two chlorobutyl rubber plungers. Thus, a total of four different combinations of semaglutide and cagrilintide formulations in dual-chamber syringes were obtained. For each combination, the "ejection experiment" described in detail in Example 3 was performed, and the number of individual particles of size >10 μm and size >25 μm (ECD) was obtained with the MFI equipment and software (normalised to counts per ml analysed liquid).

The results, given as ranges of particle counts per ml, for each of the phosphate concentrations investigated, are provided in Table 5-1.

TABLE 5-1

Measured number of particles per ml for each ejection experiment measured with MFI.

| Phosphate concentration semaglutide formulation in the 4.8 mg/ml | Number (range) of particles counted, per ml analysed liquid | |
|---|---|---|
| | Size > 10 μm | Size > 25 μm |
| 8 mM (n = 1) | 7193 | 1376 |
| 15 mM (n = 3) | 37-141 | 4-69 |
| 20 mM (n = 3) [A)] | 45-83 | 2-18 |
| 20 mM (n = 3) [B)] | 30-65 | 2-12 |

[A)] With propylene glycol as tonicity agent

[B)] With sodium chloride as tonicity agent

To enable comparison with the background particle level of the formulations without mixing taking place, particle counts for the separate formulations, as expelled from syringes in the same manner as the ejection experiments described above, are shown in Table 5-2 (normalised to counts per ml).

TABLE 5-2

Background particle levels in each formulation (no mixing of cagrilintide and semaglutide)

| Formulation | Number of particles counted, per ml analysed liquid | |
|---|---|---|
| | Size > 10 μm | Size > 25 μm |
| Cagrilintide (n = 1) | 46 | 0 |
| Semaglutide, 8 mM phosphate, propylene glycol (n = 1) | 9 | 3 |
| Semaglutide, 15 mM phosphate, propylene glycol (n = 2) | 6-9 | 0 |
| Semaglutide, 20 mM phosphate, propylene glycol (n = 2) | 25-41 | 0-3 |
| Semaglutide, 20 mM phosphate, sodium chloride (n = 2) | 31-41 | 3-6 |

The MFI particle data in Table 5-1 show that a phosphate concentration of 8 mM in semaglutide formulations will result in clearly elevated particle counts for both particle sizes (>10 μm and >25 μm), when mixed with cagrilintide containing 5 mM glutamate as buffer.

It is also evident from the data that an increase of the phosphate concentration to 15 mM will remove most but not all sub-visible particles that form during the ejection experiment. A further increase to 20 mM phosphate results in a further lowering of the sub-visible particle count measured during the ejection experiment, with similar levels observed whether propylene glycol or sodium chloride is used as the tonicity agent. The particle levels observed with 20 mM phosphate correspond to the background levels in the present experiment (Table 5-2) and thus signify that no sub-visible particles form as a consequence of the mixing of semaglutide and cagrilintide formulations in the dual-chamber syringe.

The results of this experiment therefore show that the phosphate concentration in the semaglutide formulation at pH 7.4 should be above 15 mM, e.g. 20 mM or higher, to avoid the formation of sub-visible particles during injection in combination with a cagrilintide formulation containing 5 mM glutamate at pH 4.0 with the dual-chamber syringe.

Example 6: PK Profile Following Administration of Cagrilintide and Semaglutide Via a Prefilled Dual-Chamber Syringe Studies were conducted in LYD pigs to evaluate the PK of combining cagrilintide and semaglutide after a single s.c. administration, either via a prefilled dual chamber syringe (see FIG. 1) or via separate injections of each drug. The volumes administered were about 500 microlitres of the semaglutide formulation and about 250 microlitres of the cagrilintide formulation. Dose ranges of from 0.25 mg to 2.4 mg semaglutide and from 0.25 to 4.5 mg cagrilintide were explored.

Female cross bred domestic pigs (Danish Landrace, Yorkshire and Duroc—LYD pigs), having a body weight of approximately 80-100 kg, were used for exploring PK profiles. The low dose was dosed subcutaneously with a single dose of semaglutide/cagrilintide as monotherapy or in combination using either a prefilled dual chamber syringe or as separate injections at different injections sites using the NovoPen 4 penfill (Novo Nordisk A/S). Before dosing the high doses of semaglutide/cagrilintide, the LYD pigs were dose-escalated with liraglutide, for 10 days, to avoid an initial gastro-intestinal tract related discomfort from an acute high dose of semaglutide. On day 11, the animals were dosed with semaglutide/cagrilintide as described above.

A full plasma concentration-time profile was obtained from each animal, from pre-dosing to 18 days post dosing.

Plasma was analysed by means of Luminescence Oxygen Channelling Immunoassay (LOCI) and Liquid Chromatography-Mass Spectrometry (LCMS) for semaglutide and cagrilintide, respectively. Non-compartmental pharmacokinetic analysis, using individual plasma concentration-time profiles, was performed.

TABLE 6

Comparison of PK parameters of semaglutide after co-dosing of semaglutide/cagrilintide 2.4 mg/4.5 mg using separate injections versus using a prefilled dual chamber syringe (mean ± SD)

| Group | Semaglutide Cmax (nmol/L) [mean ± SD] | Cagrilintide Cmax (nmol/L) [mean ± SD] | Semaglutide AUC/Dose (hr * kg/L) [mean ± SD] | Cagrilintide AUC/Dose (hr * kg/L) [mean ± SD] | Semaglutide t½ (hr) [mean ± SD] | Cagrilintide t½ (hr) [mean ± SD] |
|---|---|---|---|---|---|---|
| Mono | 124 ± 23.6 | 42.0 ± 4.54 | 1380 ± 78.1 | 1160 ± 75.5 | 46.5 ± 4.38 | 87.8 ± 6.93 |
| Dual chamber syringe 2.4/2.4 | 151 ± 33.4 | 69.3 ± 11.8 | 1560 ± 229 | 1690 ± 300 | 46.5 ± 4.14 | 88.3 ± 6.38 |
| % increase (Co-dosing vs. dual-chamber syringe) | ~22% | ~65% | ~13% | ~45% | ~0% | ~0.6% |

A moderate difference in semaglutide PK parameters, Cmax and tmax, was observed with the different administration methods. For cagrilintide $C_{max}$ was increased up to 65% and AUC increased up to 45% following administration of 2.4/2.4 semaglutide/cagrilintide with a prefilled dual chamber syringe, as opposed to when administered with semaglutide via two different devices.

These non-clinical data may indicate an improved effect when semaglutide and cagrilintide are administered in a single injection using a dual-chamber syringe; as opposed to when they are dosed separately, using individual syringes such as the NovoPen 4 penfill.

Example 7: AM833 (Cagrilintide) and Semaglutide Phase 1 Combination Trial

Trial Design

A 20-week, multiple ascending dose phase 1 trial investigated the safety, tolerability, pharmacokinetics and weight loss potential of AM833 (cagrilintide) administered in combination with 2.4 mg semaglutide. In the trial, six different cagrilintide doses (0.16 mg, 0.3 mg, 0.6 mg, 1.2 mg, 2.4 mg and 4.5 mg per week) were administered with semaglutide (2.4 mg per week), as separate subcutaneous injections to six separate cohorts. Subjects were randomised 3:1 to receive cagrilintide+2.4 mg semaglutide or placebo+2.4 mg semaglutide. A 16-week dose-escalation period was applied followed by 4 weeks at the target dose. 80 adults with an initial BMI between 27.0 and 39.9 kg/$m^2$ (both inclusive) completed the trial.

The trial investigated the number of treatment-emergent adverse events (primary endpoint). AM833 was well-tolerated, with the most common adverse events being injection site reactions and gastrointestinal disorders, including nausea and vomiting, the majority being non-serious and mild or moderate in severity. Surprisingly, the level of gastrointestinal disorders observed for the combination of AM833 and semaglutide in the trial was comparable to what is generally seen for glucagon-like peptides-1 (GLP-1) in monotherapy.

Results

From a mean baseline body weight of 95.7 kg, body weight decreased in all treatment arms over the 20-week treatment period, with substantial weight loss observed in subjects receiving the three highest doses of cagrilintide (1.2 mg, 2.4 mg and 4.5 mg)+2.4 mg semaglutide compared to placebo+2.4 mg semaglutide (FIG. 5).

After 20 weeks of treatment, there was a statistically significant treatment difference for mean change from baseline to end of treatment in body weight for the three highest doses of cagrilintide (1.2 mg, 2.4 mg and 4.5 mg) in combination with semaglutide, in comparison to placebo+semaglutide. The estimated mean body weight change from baseline to end of treatment were 15.6% for cagrilintide 1.2 mg, 17.0% for cagrilintide 2.4 mg and 15.6% for cagrilintide 4.5 mg; all in combination with 2.4 mg of semaglutide. A weight loss of 9.8% was observed for placebo+semaglutide. Treatment differences were not statistically significant for the three lowest doses of cagrilintide (0.16 mg, 0.3 mg and 0.6 mg) in combination with semaglutide, when compared to placebo in combination with 2.4 mg semaglutide. In all treatment arms there was evidence of body weight regain following cessation of the use of trial products at Week 20.

The invention claimed is:

1. A method of treating obesity or overweight in a subject in need thereof, comprising administering a fixed-dose combination of 0.025-5.0 mg cagrilintide and 0.05-5.0 mg semaglutide subcutaneously in a single injection.

2. The method of claim 1, wherein said subject has an initial body mass index (BMI) of 30 kg/m2 or greater.

3. The method of claim 1, wherein said subject has an initial body mass index (BMI) of 27 kg/m2 or greater.

4. The method of claim 1, wherein said subject has at least one weight-related co-morbidity.

5. The method of claim 4, wherein the weight-related comorbidity is selected from the group consisting of hypertension, diabetes, dyslipidaemia, high cholesterol and obstructive sleep apnoea.

6. The method of claim 4, wherein the weight-related comorbidity is one or a combination of the diseases selected from the group consisting of diabetes, cardiovascular disease, non-alcoholic fatty liver disease (NAFLD), and non-alcoholic steatohepatitis (NASH).

7. The method of claim 1, wherein the ratio (in mg) of cagrilintide to semaglutide is about 1:1.

8. The method of claim 1, wherein the dose of cagrilintide administered is 0.25 mg, 0.5 mg, 1.0 mg, 1.2 mg, 1.7 mg, 2.4 mg or 4.5 mg.

9. The method of claim 1, wherein the dose of semaglutide administered is 0.25 mg, 0.5 mg, 1.0 mg, 1.7 mg or 2.4 mg.

10. The method of claim 1, wherein the dose of cagrilintide administered is 0.25 mg and the dose of semaglutide administered is 0.25 mg.

11. The method of claim 1, wherein the dose of cagrilintide administered is 0.5 mg and the dose of semaglutide administered is 0.5 mg.

12. The method of claim 1, wherein the dose of cagrilintide administered is 1.0 mg and the dose of semaglutide administered is 1.0 mg.

13. The method of claim 1, wherein the dose of cagrilintide administered is 1.7 mg and the dose of semaglutide administered is 1.7 mg.

14. The method of claim 1, wherein the dose of cagrilintide administered is 2.4 mg and the dose of semaglutide administered is 2.4 mg.

15. The method of claim 1, wherein the cagrilintide and semaglutide formulations are administered, in a single injection, approximately once weekly.

16. The method of claim 15, wherein the ratio (in mg) of cagrilintide to semaglutide is about 1:1 and wherein the dose of cagrilintide administered is 0.25 mg, 0.5 mg, 1.0 mg, 1.2 mg, 1.7 mg, or 2.4 mg and the dose of semaglutide administered is 0.25 mg, 0.5 mg, 1.0 mg, 1.7 mg or 2.4 mg.

17. A method of treating obesity or overweight in a subject in need thereof, comprising administering subcutaneously in a single injection 0.25 mg cagrilintide and 0.25 mg semaglutide once a week for four weeks (weeks 0-3);

0.5 mg cagrilintide and 0.5 semaglutide once a week for four weeks (weeks 4-7);

1.0 mg cagrilintide and 1.0 semaglutide once a week for four weeks (weeks 8-11);

1.7 mg cagrilintide and 1.7 mg semaglutide once a week for four weeks (weeks 12-15); and 2.4 mg cagrilintide and 2.4 mg semaglutide mg once a week thereafter.

18. The method of claim 17, wherein said subject has an initial body mass index (BMI) of 30 kg/m2 or greater.

19. The method of claim 17, wherein said subject has an initial body mass index (BMI) of 27 kg/m2 or greater.

20. The method of claim 17, wherein said subject has at least one weight-related co-morbidity.

21. The method of claim 20, wherein the weight-related comorbidity is selected from the group consisting of hypertension, diabetes, dyslipidaemia, high cholesterol and obstructive sleep apnoea.

22. The method of claim 20, wherein the weight-related comorbidity is one or a combination of the diseases selected from the group consisting of diabetes, cardiovascular disease, non-alcoholic fatty liver disease (NAFLD), and non-alcoholic steatohepatitis (NASH).

23. A method of treating diabetes or delaying diabetes progression, or delaying or reducing the development of a major adverse cardiovascular event (MACE), or treating non-alcoholic fatty liver disease (NAFLD) or non-alcoholic steatohepatitis (NASH) in a subject in need thereof, comprising administering a fixed-dose combination of 0.025-5.0 mg cagrilintide and 0.05-5.0 mg semaglutide subcutaneously in a single injection.

24. The method of claim 23, wherein diabetes is type 2 diabetes.

25. The metho of claim 23, wherein MACE is selected from the group consisting of cardiovascular death, non-fatal myocardial infarction, non-fatal stroke, revascularisation, hospitalization for unstable angina pectoris, and hospitalization for heart failure.

* * * * *